UNITED STATES PATENT

(12) United States Patent
Yang et al.

(10) Patent No.: US 12,428,478 B2
(45) Date of Patent: Sep. 30, 2025

(54) ANTI-CLAUDIN 18.2 ANTIBODY AND APPLICATION THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Yang Yang, Shanghai (CN); Hu Ge, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1035 days.

(21) Appl. No.: 17/442,939

(22) PCT Filed: Mar. 31, 2020

(86) PCT No.: PCT/CN2020/082369
§ 371 (c)(1),
(2) Date: Sep. 24, 2021

(87) PCT Pub. No.: WO2020/200196
PCT Pub. Date: Oct. 8, 2020

(65) Prior Publication Data
US 2022/0185881 A1 Jun. 16, 2022

(30) Foreign Application Priority Data
Apr. 1, 2019 (CN) .......................... 201910257853.6

(51) Int. Cl.
C07K 16/28 (2006.01)
A61K 47/68 (2017.01)
A61P 35/00 (2006.01)
C07K 16/46 (2006.01)

(52) U.S. Cl.
CPC .......... C07K 16/28 (2013.01); A61K 47/6849 (2017.08); A61P 35/00 (2018.01); C07K 16/467 (2013.01); C07K 2317/24 (2013.01); C07K 2317/565 (2013.01); C07K 2317/567 (2013.01); C07K 2317/732 (2013.01); C07K 2317/92 (2013.01)

(58) Field of Classification Search
CPC .. C07K 16/28; C07K 16/467; C07K 2317/24; C07K 2317/565; C07K 2317/567; C07K 2317/732; C07K 2317/92; C07K 2317/77; C07K 16/30; C07K 2317/51; C07K 2317/515; C07K 2317/52; C07K 2317/56; C07K 2317/73; A61K 47/6849; A61K 2039/505; A61P 35/00; A61P 35/02; G01N 33/574
See application file for complete search history.

(56) References Cited

FOREIGN PATENT DOCUMENTS

| EP | 3483182 A1 | 5/2019 |
|---|---|---|
| WO | 2013167259 | 11/2013 |
| WO | 2013174510 A1 | 11/2013 |
| WO | 2016166122 A1 | 10/2016 |

OTHER PUBLICATIONS

Singh, P., Toom, S. & Huang, Y. Anti-claudin 18.2 antibody as new targeted therapy for advanced gastric cancer. J Hematol Oncol 10, 105 (2017) (Year: 2017).*
Kang et al. Rapid formulation development for monoclonal antibodies. BioProcess Int, 14(4): 40-45 (2016). (Year: 2016).*
Gershoni et al. Epitope mapping: the first step in developing epitope-based vaccines. BioDrugs. 2007;21(3):145-56. (Year: 2007).*
Blythe et al. Benchmarking B cell epitope prediction: underperformance of existing methods. Protein Sci. Jan. 2005;14(1):246-8. (Year: 2005).*
Schreiber et al. 3D-Epitope-Explorer (3DEX): localization of conformational epitopes within three-dimensional structures of proteins. J Comput Chem. Jul. 15, 2005;26(9):879-87. (Year: 2005).*
Ladner RC. Mapping the epitopes of antibodies. Biotechnol Genet Eng Rev. 2007;24:1-30. (Year: 2007).*
Sahin et al. Claudin-18 splice variant 2 is a pan-cancer target suitable for therapeutic antibody development. Clin Cancer Res. Dec. 1, 2008;14(23):7624-34. (Year: 2008).*

* cited by examiner

Primary Examiner — Julie Wu
Assistant Examiner — Amber K Faust
(74) Attorney, Agent, or Firm — Morgan, Lewis & Bockius LLP

(57) ABSTRACT

The present disclosure relates to an anti-Claudin 18.2 antibody and an application thereof. Specifically, the present invention relates to an anti-Claudin 18.2 antibody; a mouse-derived antibody, chimeric antibody, humanized antibody and antigen-binding fragment thereof which contain a CDR of the anti-Claudin 18.2 antibody, and a use thereof as a medicine. In particular, the present disclosure relates to a use of the anti-Claudin 18.2 antibody in the preparation of a drug for treating Claudin 18.2 positive diseases or disorders.

17 Claims, 3 Drawing Sheets
Specification includes a Sequence Listing.

ANTI-CLAUDIN 18.2 ANTIBODY AND APPLICATION THEREOF

CROSS-REFERENCE TO RELATED APPLICATIONS

The present application is the national stage of International Patent Application No. PCT/CN2020/082369, filed on Mar. 31, 2020, which claims the benefit of and priority to Chinese Application No. 201910257853.6 filed on Apr. 1, 2019, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 2, 2025, is named "702029CPUS_126268-5024-US_Sequence_Listing.TXT" and is 92,652 bytes in size.

FIELD OF THE INVENTION

The present disclosure relates to the field of antibody drugs. Specifically, the present disclosure relates to Claudin 18.2 antibodies and applications thereof.

BACKGROUND OF THE INVENTION

The descriptions herein only provide background information about the present disclosure, and do not necessarily constitute prior art.

Claudin-18 (CLDN18) is a protein encoded by the human Claudin18 gene and belongs to the tight junction protein family in cells. Claudin-18 can control the flow of molecules between layers of cells.

Claudin-18 protein structurally includes four transmembrane regions and two extracellular loops, with the N-terminus and C-terminus present inside the cytoplasm.

Claudin-18 has two splicing variants, Claudin 18.1 and Claudin 18.2. The two sequences differ from each other only in the eight amino acids in the first extracellular loop. Claudin 18.1 is expressed and distributed differently from Claudin 18.2. Claudin 18.1 is selectively expressed in normal lung cells, whereas the expression of Claudin 18.2 is highly limited in normal cells, but frequently ectopically activated and over-expressed in a variety of tumors (gastric cancer, lung cancer, pancreatic cancer, etc.). Claudin 18.2 is considered as a potential therapeutic target for gastric cancer and other types of cancer. The discovery of this target also provides a new option for the treatment of gastric cancer.

SUMMARY OF THE INVENTION

The present disclosure provides an anti-Claudin 18.2 antibody.

In some embodiments, the anti-Claudin 18.2 antibody as described above, comprises a heavy chain variable region and a light chain variable region, wherein:
  i) the heavy chain variable region comprises the same HCDR1, HCDR2 and HCDR3 sequence as those in the heavy chain variable region as shown in SEQ ID NO: 3, and the light chain variable region comprises the same LCDR1, LCDR2, and LCDR3 sequence as those in the light chain variable region as shown in SEQ ID NO: 4; or
  ii) the heavy chain variable region comprises the same HCDR1, HCDR2 and HCDR3 sequence as those in the heavy chain variable region as shown in SEQ ID NO: 5, and the light chain variable region comprises the same LCDR1, LCDR2, and LCDR3 sequence as those in the light chain variable region as shown in SEQ ID NO: 6. In some embodiments, the anti-Claudin 18.2 antibody as described above, comprises a heavy chain variable region and a light chain variable region, wherein:
  iii) the heavy chain variable region comprises HCDR1, HCDR2 and HCDR3 as shown in SEQ ID NO: 9, SEQ ID NO: 10 and SEQ ID NO: 11, respectively, and the light chain variable region comprises LCDR1, LCDR2 and LCDR3 as shown in NO: 12, SEQ ID NO: 13 and SEQ ID NO: 14, respectively; or
  iv) the heavy chain variable region comprises HCDR1, HCDR2 and HCDR3 as shown in SEQ ID NO: 15, SEQ ID NO: 16 and SEQ ID NO: 17, respectively, and the light chain variable region comprises LCDR1, LCDR2 and LCDR3 as shown in NO: 18, SEQ ID NO: 19 and SEQ ID NO: 20, respectively.

Those skilled in the art should understand that the item numbers, such as i), ii), a), b), etc., are only for the purpose of making the listed technical solutions or elements clearer and being identified easily, but do not limit the following technical solutions or elements in any respect. When the same item number is used, it does not mean that the following technical solutions or elements are the same.

In some embodiments of the anti-Claudin 18.2 antibody as described above, the anti-Claudin 18.2 antibody is a murine antibody, a chimeric antibody, or a humanized antibody.

In some embodiments, the anti-Claudin 18.2 antibody as described above comprises a heavy chain variable region and a light chain variable region, wherein:
  (v) the heavy chain variable region has at least 90%, 92%, 94%, 95%, 96%, 97%, 98%, 99%, 100% identity to the heavy chain variable region as shown in SEQ ID NO: 3 or 24, and the light chain variable region has at least 90%, 92%, 94%, 95%, 96%, 97%, 98%, 99%, 100% identity to the light chain variable region as shown in SEQ ID NO: 4 or 21; or
  (vi) the heavy chain variable region has at least 90%, 92%, 94%, 95%, 96%, 97%, 98%, 99%, 100% identity to the heavy chain variable region as shown in SEQ ID NO: 5 or 31, and the light chain variable region has at least 90%, 92%, 94%, 95%, 96%, 97%, 98%, 99%, 100% identity to the light chain variable region as shown in SEQ ID NO: 6 or 28.

In some embodiments, the anti-Claudin 18.2 antibody as described above comprises a heavy chain variable region and a light chain variable region, wherein:
  (1) the amino acid sequence of the heavy chain variable region is as shown in SEQ ID NO: 3 or has at least 90% identity to SEQ ID NO: 3, and the amino acid sequence of the light chain variable region is as shown in SEQ ID NO: 4 or has at least 90% identity to SEQ ID NO: 4;
  (2) the amino acid sequence of the heavy chain variable region is as shown in SEQ ID NO: 24 or has at least 90% identity to SEQ ID NO: 24, and the amino acid sequence of the light chain variable region is as shown in SEQ ID NO: 21 or has at least 90% identity to SEQ ID NO: 21;
  (3) the amino acid sequence of the heavy chain variable region is as shown in SEQ ID NO: 5 or has at least 90% identity to SEQ ID NO: 5, and the amino acid sequence of the light chain variable region is as shown in SEQ ID NO: 6 or has at least 90% identity to SEQ ID NO: 6; or (4) the amino acid sequence of the heavy chain variable region is as shown in SEQ ID NO: 31 or has at least 90% identity to SEQ ID NO: 31, and the amino acid sequence of the light chain variable region is as shown in SEQ ID NO: 28 or has at least 90% identity to SEQ ID NO: 28.

In some embodiments of the anti-Claudin 18.2 antibody as described above, the anti-Claudin 18.2 antibody is a humanized antibody, and the humanized antibody comprises a framework region derived from a human antibody framework region or a framework region variant thereof, and the framework region variant has at most 10 back mutations on each of the human antibody light chain framework region and/or the heavy chain framework region.

In some embodiments, the human antibody heavy chain framework region is the same as the framework region of the heavy chain variable region as shown in amino acid sequence SEQ ID NO:24, or the human antibody light chain variable region is the same as the framework region of the light chain variable region as shown in amino acid sequence SEQ ID NO:21; or the human antibody heavy chain framework region is the same as the framework region of the heavy chain variable region as shown in amino acid sequence SEQ ID NO:31, or the human antibody light chain variable region is the same as the framework region of the light chain variable region as shown in amino acid sequence SEQ ID NO:28.

In some embodiments, preferably, the framework region variant comprises mutation(s) selected from the following (a) or (b):

(a) one or more amino acid back mutation(s) of 22S, 85I or 87H comprised in the light chain variable region, and/or one or more back mutation(s) selected from the group consisting of 48I, 82T and 69M comprised in the heavy chain variable region; or (b) one or more amino acid back mutation(s) selected from the group consisting of 4L and 22S comprised in the light chain variable region, and/or one or more back mutation(s) selected from the group consisting of 38K, 40R, 48I, 66K, 67A, 69, 71L and 73K comprised in the heavy chain variable region.

In some embodiments of the anti-Claudin 18.2 antibody as described above, the framework region variant comprises mutation(s) selected from the following (a-1) or (b-1):

(a-1) amino acid back mutations 22S, 85I and 87H comprised in the light chain variable region, and amino acid back mutations 48I and 82T comprised in the heavy chain variable region; or (b-1) amino acid back mutation 4L comprised in the light chain variable region.

In some embodiments of the anti-Claudin 18.2 antibody as described above, wherein:

(vii) the heavy chain variable region sequence is as shown in SEQ ID NO: 3 and the light chain variable region sequence is as shown in SEQ ID NO: 4; or (viii) the heavy chain variable region sequence is as shown in SEQ ID NO: 24, 25, 26 or 27 and the light chain variable region sequence is as shown in SEQ ID NO: 21, 22 or 23; or (ix) the heavy chain variable region sequence is as shown in SEQ ID NO: 5 and the light chain variable region sequence is as shown in SEQ ID NO: 6; or (x) the heavy chain variable region sequence is as shown in SEQ ID NO: 31, 32, 33 or 34 and the light chain variable region sequence is as shown in SEQ ID NO: 28, 29 or 30; In some embodiments of the anti-Claudin18.2 antibody as described above, the anti-Claudin18.2 antibody or antigen-binding fragment thereof comprise a heavy chain variable region and a light chain variable region as shown below:

(xi) the heavy chain variable region sequence as shown in SEQ ID NO: 31 and the light chain variable region sequence as shown in SEQ ID NO:29; or (xii) the heavy chain variable region sequence as shown in SEQ ID NO: 26 and the light chain variable region sequence as shown in SEQ ID NO: 23.

In some embodiments of the anti-Claudin 18.2 antibody as described above, the light chain variable region and the heavy chain variable region can be a combination of the light and heavy chain variable regions as shown in the following table:

TABLE 1

Combinations of the light and heavy chain variable regions of mAb1901 humanized antibody

| Variable region | VH1 | VH2 | VH3 | VH4 |
| --- | --- | --- | --- | --- |
| VL1 | VH1VL1 | VH2VL1 | VH3VL1 | VH4VL1 |
| VL2 | VH1VL2 | VH2VL2 | VH3VL2 | VH4VL2 |
| VL3 | VH1VL3 | VH2VL3 | VH3VL3 | VH4VL3 |

TABLE 2

Combinations of the light and heavy chain variable regions of mAb1902 humanized antibody

| Variable region | VH11 | VH12 | VH13 | VH14 |
| --- | --- | --- | --- | --- |
| VL11 | VH11VL11 | VH12VL11 | VH13VL11 | VH14VL11 |
| VL12 | VH11VL12 | VH12VL12 | VH13VL12 | VH14VL12 |
| VL13 | VH11VL13 | VH12VL13 | VH13VL13 | VH14VL13 |

In some embodiments of the anti-Claudin 18.2 antibody as described above, the antibody further comprises antibody constant region(s). In some specific embodiments, the heavy chain constant region of the antibody is selected from the group consisting of human IgG1, IgG2, IgG3, and IgG4 constant region(s) and variant(s) thereof, and the light chain constant region of the antibody is selected from the group consisting of human antibody kappa, lambda chain constant region(s) and variant(s) thereof. In some specific embodiments, the antibody comprises a heavy chain constant region sequence as shown in SEQ ID NO: 7 and a light chain constant region sequence as shown in SEQ ID NO: 8. In some specific embodiments, the antibody comprises a heavy chain having at least 90%, 92%, 94%, 95%, 96%, 97%, 98%, 99%, 100% identity to the amino acid sequence as shown in SEQ ID NO: 35 or 42, and a light chain having at least 90%, 92%, 94%, 95%, 96%, 97%, 98%, 99%, 100% identity to the amino acid sequence as shown in SEQ ID NO: 36 or 39; or a heavy chain having at least 90%, 92%, 94%, 95%, 96%, 97%, 98%, 99%, 100% identity to the amino acid sequence as shown in SEQ ID NO: 37 or 49, and/or a light chain having at least 90%, 92%, 94%, 95%, 96%, 97%, 98%, 99%, 100% identity to the amino acid sequence as shown in SEQ ID NO: 38 or 46.

In some embodiments, the anti-Claudin 18.2 antibody as described above comprises:

(c) a heavy chain as shown in sequence SEQ ID NO: 35 and/or a light chain as shown in sequence SEQ ID NO: 36;

(d) a heavy chain as shown in sequence SEQ ID NO: 42, 43, 44 or 45 and/or a light chain as shown in sequence SEQ ID NO: 39, 40 or 41;

(e) a heavy chain as shown in sequence SEQ ID NO: 37 and/or a light chain as shown in SEQ ID NO: 38; or (f) a heavy chain as shown in sequence SEQ ID NO: 49, 50, 51 or 52 and/or a light chain as shown in SEQ ID NO: 46, 47 or 48.

In some embodiments of the anti-Claudin 18.2 antibody as described above, the antibody competes with the anti-Claudin 18.2 antibody or antigen-binding fragment thereof as described above to bind to human Claudin 18.2.

In some embodiments, the anti-Claudin 18.2 antibody as described above comprises:

a heavy chain as shown in amino acid sequence SEQ ID NO: 44, and a light chain as shown in sequence SEQ ID NO: 41; or a heavy chain as shown in amino acid sequence SEQ ID NO: 49, and a light chain as shown in sequence SEQ ID NO: 47.

Another aspect of the present disclosure also provides a nucleic acid molecule that encodes the anti-Claudin 18.2 antibody as described above.

Another aspect of the present disclosure also provides an expression vector comprising the nucleic acid molecule as described above.

Another aspect of the present disclosure also provides a host cell, which comprises the nucleic acid molecule as described above or the expression vector as described above, preferably the cell is a bacterial cell, a fungal cell, an insect animal cell or a mammalian cell.

Another aspect of the present disclosure also provides an antibody-drug conjugate, which is formed by conjugating the anti-Claudin 18.2 antibody as described above to a cytotoxic drug.

Another aspect of the present disclosure also provides an antibody-drug conjugate, comprising or consisting of the anti-Claudin 18.2 antibody as described above covalently binding to a cytotoxic drug.

In some embodiments, the present disclosure provides a method for preparing the anti-Claudin 18.2 antibody as described above.

In some embodiments, the present disclosure provides a method for preparing the anti-Claudin 18.2 antibody-drug conjugate as described above.

In some embodiments, the present disclosure provides a pharmaceutical composition, comprising a therapeutically effective amount of the anti-Claudin 18.2 antibody as described above, or the nucleic acid molecule as described above, or the antibody-drug conjugate as described above, and one or more pharmaceutically acceptable carriers, diluents, buffers or excipients.

In some embodiments, the present disclosure provides a method for the immunoassay or detection of Claudin18.2, including a step of contacting the above-mentioned anti-Claudin18.2 antibody with a sample to be tested.

In some embodiments, the present disclosure provides use of the anti-Claudin 18.2 antibody as described above for the preparation of a reagent for the immunoassay of human Claudin18.2.

In some embodiments, the present disclosure provides the anti-Claudin 18.2 antibody as described above for use of the immunoassay or detection of Claudin18.2.

In some embodiments, the present disclosure provides a kit comprising the anti-Claudin 18.2 antibody as described above.

In some embodiments, the present disclosure provides use of the anti-Claudin 18.2 antibody as described above, or the nucleic acid molecule as described above, or the antibody-drug conjugate as described above, or the pharmaceutical composition as described above, for the preparation of a medicament of the treatment of a cancer or tumor, wherein the cancer or tumor is preferably a Claudin18.2 positive cancer or malignant tumor, more preferably is head and neck squamous cell cancer, head and neck cancer, brain cancer, glioma, glioblastoma multiforme, neuroblastoma, central nervous system cancer, neuroendocrine tumor, laryngopharyngeal carcinoma, nasopharyngeal cancer, esophageal cancer, thyroid cancer, malignant pleural mesothelioma, lung cancer, breast cancer, liver cancer, hepatocellular tumor, hepatocellular carcinoma, liver and gallbladder cancer, pancreatic cancer, gastric cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative tumor, squamous cell carcer, Ewing sarcoma, systemic light chain amyloidosis and Merkel cell carcer; the lymphoma is selected from the group consisting of Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes, and lymphoplasmacytic lymphoma; the lung cancer is selected from the group consisting of: non-small cell lung cancer and small cell lung cancer; and the leukemia is selected from the group consisting of: chronic myeloid leukemia, acute myeloid leukemia, lymphocytic leukemia, lymphoblastic leukemia, acute lymphoblastic leukemia, chronic lymphocytic leukemia, and myeloid leukemia.

In some embodiments, the present disclosure provides a method of treating a disease associated with Claudin 18.2, the method comprising administering to a subject a therapeutically effective amount of the anti-Claudin 18.2 antibody as described above, or the nucleic acid molecule as described above, or the antibody-drug conjugate as described above, or the pharmaceutical composition as described above, wherein the disease is preferably a cancer or tumor; more preferably a Claudin 18.2 positive cancer or malignant tumor, more preferably is selected from the group consisting of head and neck squamous cell cancer, head and neck cancer, brain cancer, glioma, glioblastoma multiforme, neuroblastoma, central nervous system cancer, neuroendocrine tumor, laryngopharyngeal carcinoma, nasopharyngeal cancer, esophageal cancer, thyroid cancer, malignant pleural mesothelioma, lung cancer, breast cancer, liver cancer, hepatocellular tumor, hepatocellular carcinoma, liver and gallbladder cancer, pancreatic cancer, gastric cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative tumor, squamous cell carcer, Ewing sarcoma, systemic light chain amyloidosis and Merkel cell carcer. More preferably, the lymphoma is selected from the group consisting of: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes, and lymphoplasmacytic lymphoma; the lung cancer is selected from the group consisting of: non-small cell lung cancer and small cell lung cancer; and the leukemia is selected from the group consisting of: chronic myeloid leukemia, acute myeloid leukemia, lymphocytic leukemia, lymphoblastic leukemia, acute lymphoblastic leukemia, chronic lymphocytic leukemia, and myeloid leukemia.

In some embodiments, the therapeutically effective amount refers to 0.1 mg to 3000 mg or 1 mg to 1000 mg of the anti-Claudin 18.2 antibody as described above or the antibody-drug conjugate as described above comprised in a unit dose of the composition.

In some embodiments, the present disclosure provides the anti-Claudin 18.2 antibody as described above, or the nucleic acid molecule as described above, or the antibody-drug conjugate as described above or the pharmaceutical composition as described above, for use in the treatment of a disease associated with Claudin 18.2, wherein the disease is preferably a cancer or tumor; more preferably a Claudin 18.2 positive cancer or malignant tumor, more preferably selected from the group consisting of head and neck squamous cell cancer, head and neck cancer, brain cancer, glioma, glioblastoma multiforme, neuroblastoma, central nervous system cancer, neuroendocrine tumor, laryngopharyngeal carcinoma, nasopharyngeal cancer, esophageal cancer, thyroid cancer, malignant pleural mesothelioma, lung cancer, breast cancer, liver cancer, hepatocellular tumor, hepatocellular carcinoma, liver and gallbladder cancer, pancreatic cancer, gastric cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative tumor, squamous cell carcer, Ewing sarcoma, systemic light chain amyloidosis and Merkel cell carcer. More preferably, the lymphoma is selected from the group consisting of: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes, and lymphoplasmacytic lymphoma; the lung cancer is selected from the group consisting of: non-small cell lung cancer and small cell lung cancer; and the leukemia is selected from the group consisting of: chronic myeloid leukemia, acute myeloid leukemia, lymphocytic leukemia, lymphoblastic leukemia, acute lymphoblastic leukemia, chronic lymphocytic leukemia, and myeloid leukemia.

In some embodiments, the cancer is gastric cancer, esophageal cancer, lung cancer or pancreatic cancer.

In some embodiments, the antibody or antibody-drug conjugate can as described above play a therapeutic role in the cancers with high, medium, and low expression of Claudin 18.2 as described above.

The Claudin 18.2 antibody and antibody-drug conjugate provided in the present disclosure have excellent affinity to cell surface antigens, favorable endocytic efficiency, strong tumor inhibition efficiency, and broader spectrum of pharmaceutical application, and is suitable for clinical use as a medicament.

DESCRIPTION OF THE DRAWINGS

FIG. 3A shows the detection of ADCC effect of antibodies on wild-type NUGC4 cells (with low expression of Claudin18.2); FIG. 3B shows detection of ADCC effect of antibodies on NUGC4 cells with medium expression of Claudin18.2; FIG. 3C shows detection of ADCC effect of antibodies on NUGC4 cells with high expression of Claudin18.2.

DETAILED DESCRIPTION OF THE INVENTION

Terminology

Figure 1:
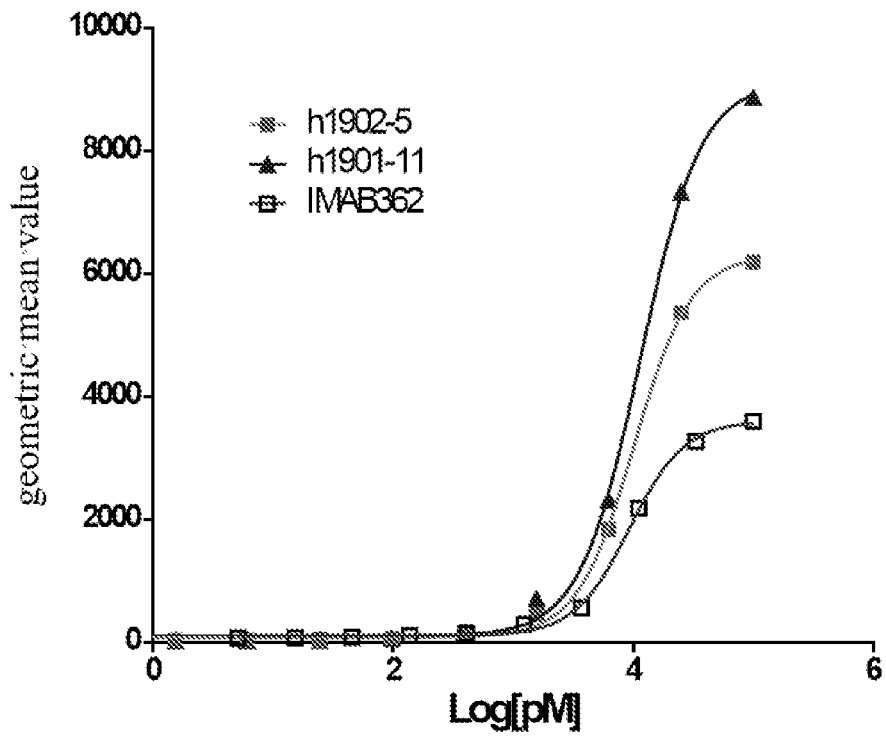
FIG. 1: the FACS test results of the binding of humanized antibodies to human Claudin 18.2 at the cellular level.

In order to make the present disclosure be more easily understood, certain technical and scientific terms are specifically defined below. Unless otherwise defined explicitly herein, all other technical and scientific terms used herein have the meaning commonly understood by those skilled in the art to which this disclosure pertains.

Three-letter codes and one-letter codes for amino acids used in the present disclosure are as described in J. biol. chem, 243, p3558 (1968).

The term "cytotoxic drug" refers to a substance that inhibits or prevents the function of cells and/or results in cell death or disruption. The cytotoxic drug involves compounds that can be used to kill cells, such as toxins, chemotherapeutics and others.

The term "toxin" refers to any substance capable of making harmful effects on the growth or proliferation of cells, and such substance can be a small molecule toxin and derivative thereof from bacteria, fungi, plants or animals, including camptothecin derivatives such as exatecan, maytansinoids and derivatives thereof (CN101573384) such as DM1, DM3, DM4, Orlistatin F (AF) and derivatives thereof, such as MMAF, MMAE, 3024 (WO 2016/127790 A1, compound 7), diphtheria toxin, exotoxin, ricin A chain, abrin A chain, modeccin, α-sarcin, *Aleutites fordii* toxic protein, dianthin toxic protein, *Phytolaca americana* toxic protein (PAPI, PAPII and PAP-S), *Momordica charantia* inhibitor, curcin, crotin, *Sapaonaria officinalis* inhibitor, gelonin, mitogellin, restrictocin, phenomycin, enomycin, and trichothecenes.

The term "chemotherapeutic drug" is a compound that can be used for the treatment of tumors. Such definition also includes antihormone agents capable of modulating, reducing, blocking, or inhibiting the hormonal effects that could promote cancer growth, and are generally in the form of systemic or systemic therapy. They can be hormones themselves. Examples of chemotherapeutic drugs include alkylating agents, such as thiotepa; cyclosphamide (CYTOXAN™); Alkyl sulfonate such as busulfan, improsulfan and piposulfan; aziridine such as benaodopa, carboquone, meturedopa and uredopa; aziridine and methylamelamine including altretamine, triethylenemelamine, triethylene phosphoramide, triethylene thiophosphoramide and trimethylolomelamine; nitrogen mustards such as chlorambucil, chlornaphazine, cholophosphamide, estramustine, ifosfamide, mechlorethamine, mechlorethaminoxide; melphalan, novembichin, phenesterine, prednimustine, trofosfamide, uramustine; nitrosureas such as carmustine, chlorozotocin, fotemustine, lomustine, nimustine, ranimustine; antibiotics such as clarithromycin, actinomycin, authramycin, azaserine, bleomycin, cactinomycin, calicheamicin, carabicin, chromomycin, carzinophilin, chromomycin, actinomycin D, daunorubicin, detorubicin, 6-diazo-5-oxy-L-norleucine, doxorubicin, epirubicin, esorubicin, idarubicin, marcellomycin, mitomycin, mycophenolic acid, nogalamycin, olivomycin, peplomycin, potfiromycin, puromycin, quelamycin, rodorubicin, streptonigrin; streptozocin, tubercidin, ubenimex, zinostatin, zorubicin; antimetabolites such as methotrexate, 5-FU; folic acid analogs such as denopterin, methotrexate, pteropterin, trimetrexate; methotrexate analogs such as fludarabine, 6-mercaptopterin, thiomethopterin, thioguanopterin; pyrimidine analogs such as ancitabine, azacitidine, 6-azuridine, carmofur, cytarabine, dideoxyuridine, doxituridine, enocitabine, fluorouridine, 5-FU; androgens such as calusterone, dromostanolong propionate, epitiostanol, mepitiostane, testolactone; anti-adrenergic agents such as aminoglutethimide, mitotane, trilostane; folic acid supplements such as frolinic acid; glucurone; aldophosphamideglycoside; aminolevulinic acid; amsacrine; bestrabucil; biasntrene; edatraxate; defofamine; colchicine; diaziquone; elfomithine; elliptinium acetate; etoglucid; gallium nitrate; hydroxyurea; lentinan; lonidamine; mitoguazone; mitoxantrone; mopidamol; nitracrine; pintostatin; phenamet; pirarubicin; podophyllinic acid; 2-ethylhydrazide; procarbazine; PSK®; razoxane; sizofiran; spirogermanium; *Alternaria tenuis* keto acid; triimine quinone; 2,2',2"-trichlorrotriethylamine; urethan; vinblastine amide; dacarbazine; mannitol mustard; mitobronitol; dibromo *euonymus* alcohol; pipobroman; gacytosine; arabinoside ("Ara-C"); cyclophosphamide; thiotepa; taxanes such as paclitaxel (TAXOL®, Bristol-Myers Squibb Oncology, Princeton, NJ) and docetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosphate; mitomycin C; mitoxantrone; vincristine; vinorelbine; navelbine; novantrone; teniposide; daunorubicin; aminopterin; xeloda; ibandronate; CPT-11; Topoisomerase inhibitor RFS2000; Difluoromethylornithine (DMFO); Retinoic acid esperamicins; capecitabine; and pharmaceutically acceptable salts, acids or derivatives of any of the above substances. This definition also includes anti-hormonal agents that can modulate or inhibit the effect of hormones on tumors. For example, anti-estrogens include tamoxifen, raloxifene, aromatase inhibitor 4(5)-imidazole, 4-hydroxyl tamoxifen, trioxifene, keoxifene, LY117018, onapristone, and toremifene (Fareston); and anti-androgens such as flutamide, nilutamide, bicalutamide, leuprolide and goserelin; and pharmaceutically acceptable salts, acids or derivatives of any of the above substances.

As used herein, "antibody" refers to immunoglobulin, and a complete antibody is a four-peptide chain structure formed by two identical heavy chains connected to two identical light chains by interchain disulfide bond(s). Immunoglobulin heavy chain constant regions exhibit different amino acid compositions and arrangement, hence present different antigenicity. Accordingly, immunoglobulins can be divided into five types, or named as immunoglobulin isotypes, namely IgM, IgD, IgG, IgA and IgE, and the corresponding heavy chains are μ, δ, γ, α and ε, respectively. According to its amino acid composition of hinge region and the number and location of heavy chain disulfide bonds, the same type of Ig can further be divided into different sub-types, for example, IgG can be divided into IgG1, IgG2, IgG3 and IgG4. Light chains can be divided into κ or λ chain based on different constant regions. Each of the five types of Ig can have a kappa chain or a lambda chain.

About 110 amino acid sequences adjacent to the N-terminus of the antibody heavy and light chains are highly variable, known as variable regions (Fv regions); the rest of amino acid sequences close to the C-terminus are relatively stable, known as constant regions. The variable region includes 3 hypervariable regions (HVRs) and 4 framework regions (FRs) with relatively conservative sequences. The three hypervariable regions which determine the specificity of the antibody are also known as complementarity determining regions (CDRs). Each light chain variable region (VL) and each heavy chain variable region (VH) consists of three CDR regions and four FR regions, with sequential order from the amino terminus to carboxyl terminus in the following order: FR1, CDR1, FR2, CDR2, FR3, CDR3, and FR4. The three CDR regions of the light chain refer to LCDR1, LCDR2, and LCDR3, and the three CDR regions of the heavy chain refer to HCDR1, HCDR2, and HCDR3.

The antibodies of the present disclosure include murine antibodies, chimeric antibodies, and humanized antibodies.

As used herein, the term "murine antibody" refers to anti-human Claudin18.2 monoclonal antibodies prepared according to the knowledge and skills in the art. During the preparation, test subject is injected with Claudin18.2 or epitope thereof as an antigen, and then a hybridoma expressing the antibody which possesses desired sequence or functional characteristics is isolated. In a preferable embodiment of the present disclosure, the murine Claudin18.2 antibody or antigen binding fragment thereof further comprises a light chain constant region of murine κ, λ chain or variant thereof, or further comprises a heavy chain constant region of murine IgG1, IgG2, IgG3 or variant thereof.

The term "chimeric antibody", is an antibody obtained by fusing the variable region of murine antibody together with the constant region of human antibody, and such antibody can alleviate the murine antibody-induced immune response. To establish a chimeric antibody, first, a hybridoma secreting specific murine monoclonal antibody is established and variable region gene is cloned from the murine hybridoma. Then constant region gene is cloned from human antibody according to the need. The murine variable region gene is connected to the human constant region gene to form a chimeric gene, which can be subsequently inserted into an expression vector. Finally the chimeric antibody molecule will be expressed in eukaryotic or prokaryotic system. In a preferable embodiment of the present disclosure, the antibody light chain of the chimeric antibody further comprises a light chain constant region of a human kappa, lambda chain or a variant thereof. The antibody heavy chain of the Claudin18.2 chimeric antibody further comprises a heavy chain constant region of human IgG1, IgG2, IgG3, IgG4 or a variant thereof, preferably comprises a heavy chain constant region of human IgG1, IgG2 or IgG4, or comprises a heavy chain constant region of IgG1, IgG2 or IgG4 with amino acid mutation(s) (such as L234A and/or L235A mutation, and/or S228P mutation).

The term "humanized antibody", also known as CDR-grafted antibody, refers to an antibody generated by grafting the non-human CDR sequences into human antibody variable region frameworks, i.e., an antibody produced in different types of human germline antibody framework sequences. Humanized antibodies can avoid heterologous responses induced by chimeric antibodies which carry a large number of heterologous protein components. Such framework sequences can be obtained from public DNA database covering germline antibody gene sequences or published references. For example, germline DNA sequences of human heavy and light chain variable region genes can be found in "VBase" human germline sequence database, as well as in Kabat, E A, et al. 1991 Sequences of Proteins of Immunological Interest, 5th Ed. To avoid a decrease in activity caused by the decreased immunogenicity, the framework sequences in human antibody variable region can be subjected to minimal reverse mutations or back mutations to maintain the activity. The humanized antibodies of the present disclosure also refers to humanized antibodies on which CDR affinity maturation is performed by yeast display.

In an embodiment of the present disclosure, the antibody or antigen binding fragment thereof further comprises a light chain constant region derived from human or muine κ, λ chain or variant thereof, or further comprises a heavy chain constant region derived from human or murien IgG1, IgG2, IgG3, IgG4 or variant thereof; preferably comprises a heavy chain constant region derived from human IgG1, IgG2 or IgG4, or IgG1, IgG2 or IgG4 variant with amino acid mutation(s) (such as L234A and/or L235A mutation, and/or S228P mutation).

As described herein, the "variants" of the heavy chain constant region and the light chain constant region of a human antibody refer to the heavy or light chain constant region variants disclosed in the prior art that are not changed in the structure and function of the antibody variable regions. Exemplary variants include IgG1, IgG2, IgG3 or IgG4 heavy chain constant region variants obtained by site-directed engineering and amino acid substitutions on the heavy chain constant region. The specific substitutions are, for example, YTE mutation, L234A and/or L235A mutation, S228P mutation, and/or mutations resulting in a knob-into-hole structure (making the antibody heavy chain have a combination of knob-Fc and hole-Fc). These mutations have been proven to confer the antibody with new properties, without changing the function of the antibody variable region.

"Human antibody (HuMAb)", "antibody derived from human", "fully human antibody" and "completely human antibody" are used interchangeably, and could be antibodies derived from human or antibodies obtained from a genetically modified organism which has been "engineered" by any method known in the art to produce specific human antibodies in response to antigen stimulation. In some technologies, elements of human heavy and light chain loci are introduced into cell strains derived from embryonic stem cell lines, in which the endogenous heavy and light chain loci are targeted for disruption. Transgenic organisms can synthesize human antibodies specific for human antigens, and the organisms can be used to produce hybridomas that secrete human antibodies. A human antibody can also be such antibody in which the heavy and light chains are encoded by nucleotide sequences derived from one or more human DNA sources. Fully human antibodies can also be constructed by gene or chromosome transfection methods and phage display technology, or constructed from B cells activated in vitro, all of which are known in the art.

The terms "full-length antibody", "full antibody", "whole antibody" and "complete antibody" are used interchangeably herein and refer to an antibody in a substantially complete form, as distinguished from antigen-binding fragments defined below. The term specifically refers to antibodies that contain constant regions in the light and heavy chains. The "antibody" of the present disclosure includes "full-length antibodies" and antigen-binding fragments thereof.

In some embodiments, the full-length antibody of the present disclosure includes full-length antibodies formed by linking the light chain variable region and the light chain constant region, and linking the heavy chain variable region and the heavy chain constant region, as shown in the light and heavy chain combination in the table below. Those skilled in the art can select the light chain constant region and heavy chain constant region from various antibody sources according to actual needs, such as human antibody-derived light chain constant region and heavy chain constant region.

The term "antigen-binding fragment" or "functional fragment" refers to one or more fragments of the antibody that retain the ability to specifically bind to an antigen (e.g., Claudin18.2). It has been shown that fragments of a full-length antibody can be used to achieve function of antigen-binding. Examples of the binding fragments contained in the term "antigen-binding fragment" of an antibody include (i) Fab fragment, a monovalent fragment composed of VL, VH, CL and CH1 domains; (ii) F(ab')₂ fragment, a bivalent fragment formed by two Fab fragments connected by a disulfide bridge in the hinge region, (iii) Fd fragment composed of VH and CH1 domains; (iv) Fv fragment composed of the VH and VL domains of one arm of the antibody; (v) dsFv, an antigen-binding fragment formed by VH and VL via interchain disulfide bonds; and (vi) diabody, bispecific antibody and multispecific antibody containing fragments such as scFv, dsFv, and Fab. In addition, the VL domain and VH domain of the Fv fragment are linked by a synthetic linker to generate a single protein chain, which is a monovalent molecular formed by pairing the VL and VH domain (referred to as single chain Fv (scFv); see, e.g., Bird et al. (1988) Science 242: 423-426; and Huston et al (1988) Proc. Natl. Acad. Sci USA85:5879-5883). Such single chain antibodies are also included in the term of "antigen binding fragment" of an antibody. Such antibody fragments are obtained using conventional techniques known in the field, and are screened for functional fragments by using the same method as that for an intact antibody. Antigen binding portions can be produced by recombinant DNA technology or by enzymatic or chemical disruption of an intact immunoglobulin. Antibodies can be in the form of different isotypes, e.g., IgG (e.g., IgG1, IgG2, IgG3 or IgG4 subtype), IgA1, IgA2, IgD, IgE or IgM antibody.

Fab is an antibody fragment having antigen-binding activity obtained by treating an IgG antibody molecule with an enzyme having the same activity as papain.

F(ab')₂ is an antibody fragment with antigen-binding activity obtained by digesting IgG with an enzyme with the same activity as pepsin.

Fab' is an antibody fragment having antigen-binding activity obtained by cleaving the above-mentioned F(ab')₂.

In addition, the Fab' can be produced by inserting DNA encoding the Fab' fragment into an expression vector, and introducing the vector into a host.

The term "single chain antibody", "single chain Fv" or "scFv" refers to a molecule comprising an antibody heavy chain variable domain (or region; VH) connected to an antibody light chain variable domain (or region; VL) by a linker. Such scFv molecules have general structure of NH₂-VL-linker-VH-COOH or NH₂-VH-linker-VL-COOH. Other linkers that can be used in the present disclosure are described by the following documents, such as but not limited to: Holliger et al. (1993) Proc. Natl. Acad. Sci. USA 90: 6444-6448; Alfthan et al. (1995), Protein Eng. 8:725-731; Choi et al. (2001), Eur. J. Immunol. 31:94-106; Hu et al. (1996), Cancer Res. 56:3055-3061; Kipriyanov et al. (1999), J. Mol. Biol. 293:41-56 and Roovers et al. (2001), Cancer Immunol.

Diabody is an antibody fragment wherein scFv or Fab is dimerized, and it is an antibody fragment having divalent antigen binding activity. In the bivalent antigen binding activity, the two antigens could be the same or different.

Bispecific and multispecific antibody refer to an antibody that can bind to two or more antigens or antigenic determinants.

dsFv is obtained by substituting one amino acid residue in each of VH and VL with a cysteine residue, and then connecting the substituted polypeptides via a disulfide bond between the two cysteine residues. The amino acid residues to be substituted with a cysteine residue can be selected based on three-dimensional structure prediction of the antibody in accordance with known methods (e.g., Protein Engineering, 7, 697 (1994)).

The term "amino acid difference" or "amino acid mutation" refers to the amino acid changes or mutations in a protein or polypeptide variant compared to the original protein or polypeptide, including 1, 2, 3 or more amino acid insertions, deletions or substitutions on the basis of the original protein or polypeptide.

The term "antibody framework" or "FR region" refers to a part of the variable domain, either VL or VH, which serves as a scaffold for the antigen binding loops (CDRs) of this variable domain. Essentially, it is a variable domain without CDRs.

The term "complementarity determining region", "CDR" or "hypervariable region" refers to one of the six hypervariable regions present in the antibody variable domain that mainly contribute to antigen binding. Generally, there are three CDRs (HCDR1, HCDR2, HCDR3) in each heavy chain variable region, and three CDRs (LCDR1, LCDR2, LCDR3) in each light chain variable region. The amino acid sequence boundaries of CDRs can be determined by any of a variety of well-known schemes, including the "Kabat" numbering criteria (see Kabat et al. (1991), "Sequences of Proteins of Immunological Interest", 5th edition, Public Health Service, National Institutes of Health, Bethesda, MD), "Chothia" numbering criteria (see Al-Lazikani et al., (1997) JMB 273:927-948) and ImmunoGenTics (IMGT) numbering criteria (Lefranc MP, Immunologist, 7, 132-136 (1999); Lefranc, MP, etc., Dev. Comp. Immunol., 27, 55-77 (2003), and the like. For example, for the classical format, following the Kabat criteria, the CDR amino acid residues in the heavy chain variable domain (VH) are numbered as 31-35 (HCDR1), 50-65 (HCDR2) and 95-102 (HCDR3); and the CDR amino acid residues in the light chain variable domain (VL) are numbered as 24-34 (LCDR1), 50-56 (LCDR2), and 89-97 (LCDR3). Following the Chothia criteria, the CDR amino acid residues in VH are numbered as 26-32 (HCDR1), 52-56 (HCDR2) and 95-102 (HCDR3); and the amino acid residues in VL are numbered as 26-32 (LCDR1), 50-52 (LCDR2) and 91-96 (LCDR3). By combining both Kabat and Chothia to define CDRs, the CDRs are composed of amino acid residues 26-35 (HCDR1), 50-65 (HCDR2) and 95-102 (HCDR3) in the human VH and amino acid residues 24-34 (LCDR1), 50-56 (LCDR2) and 89-97 (LCDR3) in the human VL. Following IMGT criteria, the CDR amino acid residues in VH are roughly numbered as 26-35 (CDR1), 51-57 (CDR2) and 93-102 (CDR3), and the CDR amino acid residues in VL are roughly numbered as 27-32 (CDR1), 50-52 (CDR2) and 89-97 (CDR3). Following IMGT criteria, the CDR regions of an antibody can be determined by using IMGT/DomainGap Align Program.

The term "epitope" or "antigenic determinant" refers to a site on an antigen to which an immunoglobulin or antibody binds (e.g., a specific site on Claudin18.2 molecule). Epitopes typically include at least 3, 4, 5, 6, 7, 8, 9, 10, 11, 12, 13, 14 or 15 contiguous or non-contiguous amino acids in a unique tertiary conformation. See, for example, Epitope Mapping Protocols in Methods in Molecular Biology, Vol. 66, G. E. Morris, Ed. (1996).

The term "specifically bind to", "selectively bind to", "selective binding" or "specific binding" refers to the binding of an antibody to a predetermined epitope on an antigen. Typically, the antibody binds with an affinity (KD) of less than about $10^{-8}$M, for example, less than about $10^{-9}$ M, $10^{-10}$ M, $10^{-11}$ M, $10^{-12}$ M or even less.

The term "KD" refers to the dissociation equilibrium constant for particular antibody-antigen interaction. Generally, the antibody of the present disclosure binds to Claudin 18.2 or epitope thereof with a dissociation equilibrium constant (KD) of less than about $10^{-7}$ M, for example, less than about $10^{-8}$ M or $10^{-9}$ M, for example, the affinity of the antibody in the present disclosure to the cell surface antigen was determined by measuring KD value with FACS method.

When the term "competition" is used in the context of antigen binding proteins that compete for the same epitope, it means that competition occurs between the antigen binding proteins, which is determined by the assays wherein an antigen binding protein to be tested (e.g., an antibody or functional fragment thereof) prevents or inhibits (e.g., reduces) the specific binding of a reference antigen binding protein (e.g., a ligand or reference antibody) to a common antigen (e.g., a Claudin18.2 antigen or fragment thereof). Numerous types of competitive binding assays are available to determine whether an antigen binding protein competes with another. These assays are, for example, solid phase direct or indirect radioimmunoassay (RIA), solid phase direct or indirect enzyme immunoassay (EIA), Sandwich competition assay (see, e.g., Stahli et al, 1983, Methods in Enzymology 9: 242-253); solid phase direct biotin-avidin EIA (see, e.g., Kirkland et al, 1986, J. Immunol. 137: 3614-3619), solid phase direct labeling assay, solid phase direct labeling sandwich assay (see, e.g., Harlow and Lane, 1988, Antibodies, A Laboratory Manual, Cold Spring Harbor Press); solid phase direct labeling RIA with 1-125 label (see, e.g., Morel et al, 1988, Molec. Immunol. 25: 7-15); solid phase direct biotin-avidin EIA (see, e.g., Cheung, et al, 1990, Virology 176: 546-552); and direct labeling RIA (Moldenhauer et al, 1990, Scand. J. Immunol. 32: 77-82). Typically, the assay involves the use of a purified antigen capable of binding to a solid surface or cell which is loaded with both an unlabeled test antigen binding protein and a labeled reference antigen binding protein. Competitive inhibition is determined by measuring the amount of label bound to the solid surface or to the cell in the presence of the test antigen binding protein. Usually, the test antigen binding protein is present in excess. Antigen binding proteins identified by competitive assay (competing with the antigen binding protein) includes: antigen binding proteins that bind to the same epitope as the reference antigen binding protein; and antigen binding proteins that bind to an epitope that is sufficiently close to the epitope to which the reference antigen binding protein binds, where the two epitopes spatially interfere with each other to hinder the binding. Additional details regarding methods for determining competitive binding are provided in the Examples herein. Typically, when a competing antigen binding protein is present in excess, it will inhibit (e.g., reduce) at least 40-45%, 45-50%, 50-55%, 55-60%, 60-65%, 65-70%, 70-75% or 75% or even more of the specific binding of the reference antigen binding protein to the common antigen. In some cases, the binding is inhibited by at least 80-85%, 85-90%, 90-95%, 95-97%, or 97% or even more.

As used herein, the term "nucleic acid molecule" refers to DNA molecules and RNA molecules. The nucleic acid molecule can be single-stranded or double-stranded, and is preferably double-stranded DNA or single-stranded mRNA or modified mRNA. A nucleic acid is "operably linked" when it is placed into a functional relationship with another nucleic acid sequence. For instance, a promoter or enhancer is operably linked to a coding sequence if it affects the transcription of the coding sequence.

Amino acid sequence "identity" refers to the percentage of the amino acid residues that are identical between the first and the second sequence when the amino acid sequences are aligned (introducing gaps when necessary) to achieve the maximum percentage of sequence identity, and any conservative substitution is not considered as part of the sequence identity. In order to determine the percentage of amino acid sequence identity, the alignment can be achieved in a variety of ways within the scope of the art, for example, using publicly available computer software, such as BLAST, BLAST-2, ALIGN, ALIGN-2 or Megalign (DNASTAR) software. Those skilled in the art can determine the parameters suitable for measuring the alignment, including any algorithm required to achieve the maximum alignment over the entire length of the sequences being compared.

The term "expression vector" refers to a nucleic acid molecule capable of transporting another nucleic acid to which it has been linked. In one embodiment, the vector is a "plasmid," which refers to a circular double stranded DNA loop into which additional DNA segments could be ligated. In another embodiment, the vector is a viral vector, wherein additional DNA segments could be ligated into the viral genome. The vectors disclosed herein are capable of self-replicating in the host cell into which they are introduced (e.g., bacterial vectors having a bacterial replication origin and episomal mammalian vectors), or could be integrated into the genome of a host cell upon introduction into the host cell, and thereby are replicated along with the host genome (e.g., non-episomal mammalian vectors).

Methods for producing and purifying antibodies and antigen-binding fragments are well known in the art, for example, Antibodies: a Laboratory Manual, Cold Spring Harbor, New York, chapters 5-8 and 15. For example, mice can be immunized with human Claudin18.2 or fragment thereof, and the resulting antibodies can then be renatured, purified, and sequenced for amino acid sequences by using conventional methods well known in the art.

Antigen-binding fragments can also be prepared by conventional methods. The antibodies or antigen binding fragments of the present disclosure are engineered to incorporate one or more human framework regions onto the CDR regions derived from non-human antibody. Human FR germline sequences can be obtained from ImMunoGeneTics (IMGT) via website, or from The Immunoglobulin Facts Book, 2001, ISBN 012441351, by aligning against IMGT human antibody variable germline gene database using MOE software.

The term "host cell" refers to a cell into which an expression vector has been introduced. Host cells could include bacterial, microbial, plant or animal cells. Bacteria susceptible to be transformed include members of the enterobacteriaceae such as *Escherichia coli* or *Salmonella* strains; *Bacillaceae* such as *Bacillus subtilis*; *Pneumococcus*; *Streptococcus* and *Haemophilus influenzae*. Suitable microorganisms include *Saccharomyces cerevisiae* and *Pichia pastoris*. Suitable animal host cell lines include CHO (Chinese Hamster Ovary Cell Line), 293 cells and NS0 cells.

The antibodies or antigen-binding fragments of the present disclosure can be prepared and purified by conventional methods. For example, the cDNA sequences encoding the heavy and light chains can be cloned and recombined into a expression vector. The recombinant immunoglobulin expression vector can be stably transfected into host cells. As a more recommended prior art, mammalian expression systems can lead to glycosylation of the antibodies, especially in the highly conserved N-terminal sites of the Fc region. Stable clones were obtained by expressing an antibody specifically binding to human Claudin 18.2. Positive clones could be expanded in bioreactors for antibody production. Culture medium, into which an antibody has been secreted, can be purified by conventional techniques. For example, purification can be performed on Protein A or G Sepharose FF column that has been adjusted with buffer. The nonspecific binding components are washed out. The bound antibody is eluted by pH gradient and antibody fragments are detected by SDS-PAGE, and then pooled. The antibodies can be filtered and concentrated using common techniques. Soluble mixtures and multimers can be effectively removed by common techniques, such as size exclusion or ion exchange. The resulting product is then immediately frozen, for example at −70° C., or could be lyophilized.

"administration", "dosing" or "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration", "dosing" or "treatment" can refer, e.g., to therapeutic, pharmacokinetic, diagnostic, research, and experimental methods. The treatment of a cell encompasses contacting a reagent with the cell, as well as contacting a reagent with a fluid, the fluid in turn is in contact with the cell. "Administration", "dosing" or "treatment" also means in vitro or ex vivo treatments, e.g., of a cell, with a reagent, diagnostic, binding compound, or with another cell. "Treatment", as it applies to a human, veterinary, or research subject, refers to therapeutic treatment, prophylactic or preventative measures, research and diagnostic applications.

"Treat" means administration of a therapeutic agent, such as a composition comprising any of the antibodies or antigen binding fragments of the present disclosure, internally or externally to a patient having one or more disease symptoms for which the therapeutic agent has known therapeutic activity. Typically, the agent is administered in an amount effectively to alleviate one or more disease symptoms in the patient or population to be treated, to induce the regression of or inhibit the progression of such symptom(s) by any clinically measurable degree. The amount of a therapeutic agent that is effective to alleviate any particular disease symptom (also referred to as the "therapeutically effective amount") can vary according to various factors such as the disease state, age, and body weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present disclosure (e.g., a treatment method or article of manufacture) may not be effective in alleviating the target disease symptom(s) in every patient, it should alleviate the target disease symptom(s) in a statistically significant number of patients as determined by any statistical test known in the art such as Student's t-test, chi-square test, U-test according to Mann and Whitney, Kruskal-Wallis test (H-test), Jonckheere-Terpstra-test and Wilcoxon-test.

"Conservative modification" or "conservative substitution or replacement" refers to substitutions of amino acids in a protein with other amino acids having similar characteristics (e.g. charge, side-chain size, hydrophobicity/hydrophilicity, backbone conformation and rigidity, etc.), such that the changes can frequently occur without altering the biological activity of the protein. Those skilled in the art understand that, generally, a single amino acid substitution in a non-essential region of a polypeptide does not substantially change the biological activity (see, for example, Watson et al. (1987) Molecular Biology of the Gene, The Benjamin/Cummings Pub. Co., Page 224, 4th edition). In addition, substitutions with structurally or functionally similar amino acids are less likely to disrupt biological activity. Exemplary conservative substitutions are set forth in the table below, "Exemplary Amino Acid Conservative Substitutions".

TABLE 3

Exemplary amino acid conservative substitutions

| Original residue | Conservative substitution |
|---|---|
| Ala (A) | Gly; Ser |
| Arg(R) | Lys; His |
| Asn (N) | Gln; His; Asp |
| Asp (D) | Glu; Asn |
| Cys (C) | Ser; Ala; Val |
| Gln(Q) | Asn; Glu |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro(P) | Ala |
| Ser(S) | Thr |
| Thr(T) | Ser |
| Trp (W) | Tyr; Phe |
| Tyr (Y) | Trp; Phe |
| Val (V) | Ile; Leu |

"Effective amount" or "effective dose" refers to the amount of a medicament, compound, or pharmaceutical composition necessary to obtain any one or more beneficial or desired results. For prophylactic applications, beneficial or desired results include elimination or reduction of risk, reduction of severity, or delay of the onset of the disease, including the biochemical, histological, and behavioral manifestations of the condition, its complications, and intermediate pathological phenotypes during the development of the condition. For therapeutic applications, beneficial or desired results include clinical results, such as reduction of the incidence of various conditions associated with target antigen of the present disclosure or improvement of one or more symptoms of the condition, reduction of the dosage of other agents required to treat the condition, enhancement of the efficacy of another agent, and/or delay of the progression of the condition associated with the target antigen of the present disclosure in patients.

"Exogenous" refers to substances produced outside organisms, cells, or humans according to circumstances.

"Endogenous" refers to substances produced in cells, organisms, or human bodies according to circumstances.

"Identity" refers to the sequence similarity between two polynucleotide sequences or between two polypeptide sequences. When a position in both of the two sequences to be compared is occupied by the same base or amino acid monomer subunit, e.g., if a position in each of two DNA molecules is occupied by adenine, then the molecules are homologous at that position. The percentage of identity between two sequences is a function of the number of matching or homologous positions shared by the two sequences divided by the number of positions to be compared and then multiplied by 100. For example, when two sequences are optimally aligned, if 6 out of 10 positions in the two sequences are matched or homologous, then the two sequences are 60% homologous; if 95 out of 100 positions in the two sequences are matched or homologous, then the two sequences are 95% homologous. Generally, when two sequences are aligned, comparison is performed to give the maximum identity percentage.

For example, the comparison can be performed by BLAST algorithm, in which the parameters of the algorithm are selected to give the maximum match between each sequence over the entire length of each reference sequence. The following references refer to the BLAST algorithm frequently used for sequence analysis: BLAST algorithm (BLAST ALGORITHMS): Altschul, S F et al., (1990) J. Mol. Biol. 215:403-410; Gish, W. et al., (1993) Nature Genet. 3:266-272; Madden, T L et al., (1996) Meth. Enzymol. 266:131-141; Altschul, S F et al., (1997) Nucleic Acids Res. 25:3389-3402; Zhang, J. et al. (1997) Genome Res. 7:649-656. Other conventional BLAST algorithms such as those available from NCBI BLAST are also well known to those skilled in the art.

As used herein, the expressions "cell," "cell line," and "cell culture" are used interchangeably and all such designations include progeny. Thus, "transformant" and "transformed cell" include the primary subject cells and cultures derived therefrom regardless of the number of passages. It should be also understood that all progeny may not be precisely identical in DNA content, due to intentional or unintentional mutations. Mutant progeny that have the same function or biological activity as screened in the originally transformed cells are included. Where distinct designations are intended to, it will be clearly understood from the context.

"Isolated" refers to that a molecule is substantially free of other biological molecules, such as nucleic acids, proteins, lipids, carbohydrates, or other materials, such as cell debris and growth medium. In general, the term "isolated" is not intended to mean the complete absence of these materials or the absence of water, buffers or salts, unless they are present in an amount that significantly interferes with the experimental or therapeutic use of the compound as described herein.

"Optional" or "optionally" means that the event or circumstance that follows could but does not necessarily occur, and the description includes the instances in which the event or circumstance does or does not occur.

"Pharmaceutical composition" refers to a mixture composition one or more compounds according to the present disclosure or a physiologically/pharmaceutically acceptable salt or produg thereof and other chemical components, such as physiologically/pharmaceutically acceptable carriers and excipients. The pharmaceutical composition aims at promoting the administration to an organism, facilitating the absorption of the active ingredient and thereby exerting a biological effect.

The term "pharmaceutically acceptable carrier" refers to any inactive substance suitable for use in a formulation for the delivery of antibodies or antigen-binding fragments. A carrier can be an anti-adhesive agent, adhesive agent, coating agent, disintegrating agent, filler or diluent, preservative (such as antioxidant, antibacterial or antifungal agent), sweetener, absorption delaying agent, wetting agent, emulsifier, buffer, and the like. Examples of suitable pharmaceutically acceptable carriers include water, ethanol, polyol (such as glycerol, propylene glycol, polyethylene glycol, and the like) dextrose, vegetable oil (such as olive oil), saline, buffer, buffered saline, and isotonic agent, such as sugars, polyol, sorbitol and sodium chloride.

In addition, the present disclosure includes an agent for treating a disease associated with target antigen (such as Claudin18.2) positive cells, the agent comprising the anti-Claudin18.2antibody or antibody-binding fragment thereof of the present disclosure as an active ingredient.

There is not particular limitation on the Claudin 18.2-related disease in the present disclosure, as long as the disease is related to Claudin 18.2. For example, the therapeutic response induced by the molecule of the present disclosure includes: (1) preventing Claudin 18.2 from binding to its receptor/ligand, through binding of molecule of the present disclosure to human Claudin 18.2, or (2) killing the tumor cells over-expressing Claudin 18.2. Therefore, the molecules of the present disclosure, when comprised in preparations and formulations suitable for therapeutic applications, are very useful for such persons who have tumors or cancers, preferably melanoma, colon cancer, breast cancer, lung cancer, gastric cancer, intestinal cancer, kidney cancer, non-small cell lung cancer, bladder cancer, etc.

In addition, the present disclosure relates to methods for immunodetection or determination of target antigens (for example, Claudin18.2), reagents for immunodetection or determination of target antigens (for example, Claudin18.2), methods for immunodetection or determination of cells expressing target antigens (for example, Claudin18.2), and the diagnostic agents for diagnosing diseases associated with target antigen (for example, Claudin18.2)-positive cells, comprising the antibody or antibody fragment of the present disclosure that specifically recognizes the target antigen (for example, human Claudin18.2) and binds to the extracellular amino acid sequences or to the tertiary structure thereof as an active ingredient.

In the present disclosure, the method for detecting or measuring the amount of the target antigen (e.g. Claudin18.2) can be any known method. For example, it includes immunoassay or immunodetection method.

The immunoassay or immunodetection method is a method of detecting or measuring the amount of an antibody or antigen with a labeled antigen or antibody. Examples of immunoassay or immunodetection methods include radioactive substance-labeled immunoantibody method (RIA), enzyme immunoassay (EIA or ELISA), fluorescence immunoassay (FIA), luminescence immunoassay, western blotting, physicochemical method, and the like.

The above-mentioned diseases related to Claudin18.2-positive cells can be diagnosed by detecting or measuring Claudin18.2-expressing cells using the antibodies or antibody fragments of the present disclosure.

Cells expressing the polypeptide can be detected by the known immunodetection methods, preferably by immunoprecipitation, fluorescent cell staining, immunotissue staining, and the like. In addition, the method such as fluorescent antibody staining method with the FMAT8100HTS system (Applied Biosystem) can be used.

In the present disclosure, there is no particular limitation on the samples to be detected or measured for the target antigen (e.g. Claudin18.2), as long as they may comprise cells expressing the target antigen (e.g. Claudin18.2), such as tissue, cells, blood, plasma, serum, pancreatic juice, urine, faeces, tissue fluid or culture medium.

Dependent on the required diagnostic method, the diagnostic agent comprising the monoclonal antibody or antibody fragment thereof of the present disclosure could also comprise reagents for performing an antigen-antibody reaction or reagents for detecting the reaction. The reagents for performing an antigen-antibody reaction include buffers, salts and the like. The reagents for detection include reagents commonly used in immunoassay or immunodetection methods, for example, a labeled secondary antibody that recognizes the monoclonal antibody, antibody fragment or conjugate thereof, and a substrate corresponding to the label.

The details of one or more embodiments of the present disclosure are set forth in the above specification. The preferred methods and materials are described below, although any method and material similar or identical to those described herein can be used in the practice or testing of the present disclosure. Through the specification and claims, other features, purposes and advantages of the present disclosure will become apparent. In the specification and claims, the singular forms include plural aspects unless the context clearly dictates otherwise. Unless otherwise defined explicitly herein, all technical and scientific terms used herein have the meaning commonly understood by those skilled in the art to which this disclosure belongs. All patents and publications cited in the specification are incorporated by reference. The following examples are presented to more fully illustrate the preferred embodiments of the present disclosure. These examples should not be construed as limiting the scope of the present disclosure in any way, and the scope of the present disclosure is defined by the claims.

EXAMPLES

Example 1: Construction of a Cell Line Highly Expressing Claudin 18.2

Lipofectamine 3000 transfection reagent was used to transfect the pCDH-hClaudin18.2 lentiviral expression vector plasmid and pVSV-G, pCMV-dR8.91 lentiviral system packaging vector into the virus packaging cell 293T; supernatant of the culture medium containing the virus was collected, filtered and centrifuged at an ultra-high-speed; The concentrated virus was used to infect the human gastric signet ring cell carcinoma cell line NUGC4, screened with puromycin for two to three weeks, and then sorted with FACS single cell sorting.

The expression level of Claudin 18.2 was determined according to the tumor IHC score. Cells with the expression level of Claudin 18.2 equivalent to that of tumors with IHC score of 3 are considered as high-expressing cells, and cells with the expression level of Claudi 18.2 equivalent to that of tumors with IHC score of 2 are considered as medium-expressing cells. The Claudin18.2 expression on the surface of NUGC4 cells infected with lentivirus was detected with FACS detection, and the NUGC4/hClaudin18.2 monoclonal cell lines with the highest Claudin18.2 expression were selected. At the same time, the Claudin 18.2 expression on the surface of wild-type NUGC4 cells was detected by FACS, and the NUGC4 clone cell lines with medium expression of Claudin 18.2 were selected. The wild-type NUGC4 were cells with low expression of Claudin 18.2.

The selected monoclonal cell lines were expanded and cultured, and frozen and stored for subsequent assays.

```
Claudin 18.2 Sequence Genbank: NP_001002026:
                                                          (SEQ ID NO: 1)
MAVTACQGLGFVVSLIGIAGIIAATCMDQWSTQDLYNNPVTAVFNYQGLWRS

CVRESSGFTECRGYFTLLGLPAMLQAVRALMIVGIVLGAIGLLVSIFALKCIRIGSMEDS

AKANMTLTSGIMFIVSGLCAIAGVSVFANMLVTNFWMSTANMYTGMGGMVQTVQT

RYTFGAALFVGWVAGGLTLIGGVMMCIACRGLAPEETNYKAVSYHASGHSVAYKPG

GFKASTGFGSNTKNKKIYDGGARTEDEVQSYPSKHDYV.

Claudin 18.2 DNA sequence:
                                                          (SEQ ID NO: 2)
   1 AGAATTGCGC TGTCCACTTG TCGTGTGGCT CTGTGTCGAC ACTGTGCGCC ACCATGGCCG

61 TGACTGCCTG TCAGGGCTTG GGGTTCGTGG TTTCACTGAT TGGGATTGCG GGCATCATTG

121 CTGCCACCTG CATGGACCAG TGGAGCACCC AAGACTTGTA CAACAACCCC GTAACAGCTG

181 TTTTCAACTA CCAGGGGCTG TGGCGCTCCT GTGTCCGAGA GAGCTCTGGC TTCACCGAGT

241 GCCGGGGCTA CTTCACCCTG CTGGGGCTGC CAGCCATGCT GCAGGCAGTG CGAGCCCTGA

301 TGATCGTAGG CATCGTCCTG GGTGCCATTG GCCTCCTGGT ATCCATCTTT GCCCTGAAAT

361 GCATCCGCAT TGGCAGCATG GAGGACTCTG CCAAAGCCAA CATGACACTG ACCTCCGGGA

421 TCATGTTCAT TGTCTCAGGT CTTTGTGCAA TTGCTGGAGT GTCTGTGTTT GCCAACATGC

481 TGGTGACTAA CTTCTGGATG TCCACAGCTA ACATGTACAC CGGCATGGGT GGGATGGTGC

541 AGACTGTTCA GACCAGGTAC ACATTTGGTG CGGCTCTGTT CGTGGGCTGG GTCGCTGGAG

601 GCCTCACACT AATTGGGGGT GTGATGATGT GCATCGCCTG CCGGGGCCTG GCACCAGAAG

661 AAACCAACTA CAAAGCCGTT TCTTATCATG CCTCAGGCCA CAGTGTTGCC TACAAGCCTG

721 GAGGCTTCAA GGCCAGCACT GGCTTTGGGT CCAACACCAA AAACAAGAAG ATATACGATG

781 GAGGTGCCCG CACAGAGGAC GAGGTACAAT CTTATCCTTC CAAGCACGAC TATGTGTAAT

841 GCTCTAAGAC CTCTCAGCAC GGGCGGAAGA AACTCCCGGA GAGCTCACCC AAAAAACAAG

901 GAGATCCCAT CTAGATTTCT TCTTGCTTTT GACTCACAGC TGGAAGTTAG AAAAGCCTCG

961 ATTTCATCTT TGGAGAGGCC AAATGGTCTT AGCCTCAGTC TCTGTCTCTA AATATTCCAC

1021 CATAAAACAG CTGAGTTATT TATGAATTAG AGGCTATAGC TCACATTTTC AATCCTCTAT

1081 TTCTTTTTTT AAATATAACT TTCTACTCTG ATGAGAGAAT GTGGTTTTAA TCTCTCTCTC

1141 ACATTTGAT GATTTAGACA GACTCCCCCT CTTCCTCCTA GTCAATAAAC CCATTGATGA

1201 TCTATTTCCC AGCTTATCCC CAAGAAAACT TTTGAAAGGA AAGAGTAGAC CCAAAGATGT

1261 TATTTTCTGC TGTTTGAATT TTGTCTCCCC ACCCCCAACT TGGCTAGTAA TAAACACTTA

1321 CTGAAGAAGA AGCAATAAGA GAAAGATATT TGTAATCTCT CCAGCCCATG ATCTCGGTTT

1381 TCTTACACTG TGATCTTAAA AGTTACCAAA CCAAAGTCAT TTTCAGTTTG AGGCAACCAA

1441 ACCTTTCTAC TGCTGTTGAC ATCTTCTTAT TACAGCAACA CCATTCTAGG AGTTTCCTGA

1501 GCTCTCCACT GGAGTCCTCT TTCTGTCGCG GGTCAGAAAT TGTCCCTAGA TGAATGAGAA

1561 AATTATTTTT TTTAATTTAA GTCCTAAATA TAGTTAAAAT AAATAATGTT TTAGTAAAAT

1621 GATACACTAT CTCTGTGAAA TAGCCTCACC CCTACATGTG GATAGAAGGA AATGAAAAAA

1681 TAATTGCTTT GACATTGTCT ATATGGTACT TTGTAAAGTC ATGCTTAAGT ACAAATTCCA

1741 TGAAAAGCTC ACTGATCCTA ATTCTTTCCC TTTGAGGTCT CTATGGCTCT GATTGTACAT

1801 GATAGTAAGT GTAAGCCATG TAAAAAGTAA ATAATGTCTG GCACAGTGG CTCACGCCTG

1861 TAATCCTAGC ACTTTGGGAG GCTGAGGAGG AAGGATCACT TGAGCCCAGA AGTTCGAGAC
```

-continued

```
1921 TAGCCTGGGC AACATGGAGA AGCCCTGTCT CTACAAAATA CAGAGAGAAA AAATCAGCCA

1981 GTCATGGTGG CCTACACCTG TAGTCCCAGC ATTCCGGGAG GCTGAGGTGG GAGGATCACT

2041 TGAGCCCAGG GAGGTTGGGG CTGCAGTGAG CCATGATCAC ACCACTGCAC TCCAGCCAGG

2101 TGACATAGCG AGATCCTGTC TAAAAAAATA AAAAATAAAT AATGGAACAC AGCAAGTCCT

2161 AGGAAGTAGG TTAAAACTAA TTCTTTAAAA AAAAAAAAAA GTTGAGCCTG AATTAAATGT

2221 AATGTTTCCA AGTGACAGGT ATCCACATTT GCATGGTTAC AAGCCACTGC CAGTTAGCAG

2281 TAGCACTTTC CTGGCACTGT GGTCGGTTTT GTTTTGTTTT GCTTTGTTTA GAGACGGGGT

2341 CTCACTTTCC AGGCTGGCCT CAAACTCCTG CACTCAAGCA ATTCTTCTAC CCTGGCCTCC

2401 CAAGTAGCTG GAATTACAGG TGTGCGCCAT CACAACTAGC TGGTGGTCAG TTTTGTTACT

2461 CTGAGAGCTG TTCACTTCTC TGAATTCACC TAGAGTGGTT GGACCATCAG ATGTTTGGGC

2521 AAAACTGAAA GCTCTTTGCA ACCACACACC TTCCCTGAGC TTACATCACT GCCCTTTTGA

2581 GCAGAAAGTC TAAATTCCTT CCAAGACAGT AGAATTCCAT CCCAGTACCA AAGCCAGATA

2641 GGCCCCCTAG GAAACTGAGG TAAGAGCAGT CTCTAAAAAC TACCCACAGC AGCATTGGTG

2701 CAGGGGAACT TGGCCATTAG GTTATTATTT GAGAGGAAAG TCCTCACATC AATAGTACAT

2761 ATGAAAGTGA CCTCCAAGGG GATTGGTGAA TACTCATAAG GATCTTCAGG CTGAACAGAC

2821 TATGTCTGGG GAAAGAACGG ATTATGCCCC ATTAAATAAC AAGTTGTGTT CAAGAGTCAG

2881 AGCAGTGAGC TCAGAGGCCC TTCTCACTGA GACAGCAACA TTTAAACCAA ACCAGAGGAA

2941 GTATTTGTGG AACTCACTGC CTCAGTTTGG GTAAAGGATG AGCAGACAAG TCAACTAAAG

3001 AAAAAAGAAA AGCAAGGAGG AGGGTTGAGC AATCTAGAGC ATGGAGTTTG TTAAGTGCTC

3061 TCTGGATTTG AGTTGAAGAG CATCCATTTG AGTTGAAGGC CACAGGGCAC AATGAGCTCT

3121 CCCTTCTACC ACCAGAAAGT CCCTGGTCAG GTCTCAGGTA GTGCGGTGTG GCTCAGCTGG

3181 GTTTTTAATT AGCGCATTCT CTATCCAACA TTTAATTGTT TGAAAGCCTC CATATAGTTA

3241 GATTGTGCTT TGTAATTTTG TTGTTGTTGC TCTATCTTAT TGTATATGCA TTGAGTATTA

3301 ACCTGAATGT TTTGTTACTT AAATATTAAA AACACTGTTA TCCTACAGTT.
```

Example 2: Production of Anti-Human Claudin18.2 Monoclonal Antibody

1 Immunization

Anti-human Claudin 18.2 monoclonal antibodies were produced by immunizing mice.

SJL white mice, female, 6-8 weeks old were used for experiment (Beijing Vital River Laboratory Animal Technology Co., Ltd., animal production license number: SCXK (Beijing) 2012-0001). Feeding environment: SPF level. After purchased, the mice were kept in the laboratory environment for 1 week, 12/12 hours light/dark cycle, at temperature of 20-25° C.; humidity of 40-60%. Then, the mice that had been adapted to the environment were immunized according to the following schemes. The immune antigen was huClaudin18.2-HEK293 cell (HEK-293 cell line stably transfected with human Claudin 18.2 plasmid).

Immunization protocol: Before the primary immunization with cells, mice were injected intraperitoneally (IP) with TiterMax® Gold Adjuvant (Sigma Cat No. T2684), 0.1 ml/mouse; Half an hour later, each mouse was injected intraperitoneally (IP) with cell fluid diluted to a concentration of $1\times10^8$/ml with 0.1 ml saline. After the cells were evenly dispersed by pipetting, they were inoculated on day 0, day 14, day28, day42 and day 56. Blood samples were collected on day 21, 35, 49 and 63; the antibody titer in mouse serum was determined by ELISA method. After 4 to 5 immunizations, mice with a high serum antibody titer that was tending to the plateau were selected for fusion with splenocyte. Three days before the fusion with splenocyte, $1\times10^7$ cells were injected intraperitoneally (IP) for booster immunization.

2. Fusion with Splenocyte

Hybridoma cells were obtained by fusing splenic lymphocytes with myeloma Sp2/0 cells (ATCC® CRL-8287™) by using a PEG-mediated fusion procedure. The hybridoma cells were resuspended in complete medium (IMDM medium comprising 20% FBS, 1×HAT, 1×OPI) at a density of $0.5\times10^6$ to $1\times10^6$/ml, seeded in a 96-well plate with 100 μl/well, incubated at 37° C. and 5% $CO_2$ for 3-4 days, supplemented with 100 μl/well of HAT complete medium, and maintained for another 3-4 days until formation of clones. The supernatant was removed, added with 200 μl/well of HT complete medium (IMDM medium comprising 20% FBS, 1×HT and 1×OPI), incubated at 37° C., 5% $CO_2$ for 3 days and then subjected to ELISA detection.

3 Screening of Hybridoma Cells

According to the growth density of hybridoma cells, the culture supernatant was detected by binding ELISA method. Cells that have strong binding ability to huClaudin18.2-HEK293 cells while do not bind to HEK293 cells were selected, and then expanded and cryopreserved in time;

Subcloning were performed for twice to three times until a single cell clone was obtained.

Cells after each subcloning were also tested by cell binding assay. The hybridoma clones were obtained by screening via the above assay. The antibodies were further prepared by serum-free cell culture method. The antibodies were purified according to the example of purification, and used in the test examples.

Example 3: Humanization of Murine Antibodies

The monoclonal hybridoma cell lines mAb1901 and mAb1902 with high in vitro activity were selected; the monoclonal antibody sequences were cloned, and then humanized, recombinant expressed and evaluated for activity.

The procedures of cloning the sequences from the hybridoma were as follows. Hybridoma cells in logarithmic growth phase were collected. RNAs were extracted with Trizol (Invitrogen, 15596-018) according to the instruction of kit and were reversely transcribed by PrimeScript™ Reverse Transcriptase (Takara, cat #2680A). The cDNAs resulting from reverse transcription were amplified by PCR using mouse Ig-Primer Set (Novagen, TB326 Rev. B 0503), and the amplified products were sent to a company for sequencing. The amino acid sequences corresponding to the obtained DNA sequences are shown in SEQ ID NOs: 3-6;

```
mAb1901 murine heavy chain variable region
                                    (SEQ ID NO: 3)
EVQLMESGGGLVKPGGSLKLSCAASGFTFSDYGIHWVRQAPEMGLEW

IAYISRGSSTIYYADTVKGRFTMSRDNAKNTLFLQMTSLRSEDTAMY

YCARGGYDTRNAMDYWGQGTSVTVSS.

mAb1901 murine light chain variable region
                                    (SEQ ID NO: 4)
DIVMTQSPSSLSVSAGEKVTMSCKSSQSLLNSGNQKNYLAWYQQKPG

QPPKLLIYGASTRASGVPDRFTGSGSGTDFTLTISSVQAEDLAIYHC

QNDLYYPLTFGAGTKLELK.

mAb1902 murine heavy chain variable region
                                    (SEQ ID NO: 5)
EVQLQESGAELVKPGASVKLSCKASGYIFTSYWMHWVKQRPGQGLEW

IGMIHPNSGSTNYNEKFKGKATLTLDKSSSTAYMQLSSLPSEDSAVY

YCARLKTGNSFDYWGQGTTLTVSS.

mAb1902 murine light chain variable region
                                    (SEQ ID NO: 6)
DIVLTQSPSSLTVTAGEKVTMSCKSSQSLLNSGNQKNYLTWYQQKPG

QPPKLLIYWASTRESGVPDRFTGSGSGTDFTLTISSVQAEDLAIYYC

QNAYTYPFTFGSGTKLEIK.
```

The above murine heavy and light chain variable regions were respectively linked to the human IgG1 heavy chain constant region and human kappa light chain constant region as described below, so as to form chimeric antibodies ch1901 and ch1902.

The constant region was selected from the following sequences:

```
The human IgG1 antibody heavy chain constant
region
                                    (SEQ ID NO: 7)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSV

LTVLHQDWLNGKEYKCKVSNKALPAPIEKTISKAKGQPREPQVYTLP

PSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

K.

Human kappa light chain constant region:
                                    (SEQ ID NO: 8)
RTVAAPSVFIFPPSDEQLKSGTASVVCLLNNFYPREAKVQWKVDNAL

QSGNSQESVTEQDSKDSTYSLSSTLTLSKADYEKHKVYACEVTHQGL

SSPVTKSFNRGEC.
```

The murine monoclonal antibodies were humanized as disclosed in many documents in the field. Briefly, the parental (murine antibody) constant domains were replaced with human constant domains, and human germline antibody sequences were selected based on the homology of murine and human antibodies to perform CDR grafting. In the present invention, candidate molecules with favorable activity were selected for humanization, and the results are as follows.

1. CDR Regions of Murine Antibody

The VH/VL CDR amino acid residues in table 4 were determined and annotated by the Kabat numbering criteria.

The CDR sequences of murine antibodies are shown in Table 4:

TABLE 4

| CDR sequences of murine antibodies | |
|---|---|
| Antibody | |
| mAb1901 | |
| HCDR1 | DYGIH (SEQ ID NO: 9) |
| HCDR2 | YISRGSSTIYYADTVKG (SEQ ID NO: 10) |
| HCDR3 | GGYDTRNAMDY (SEQ ID NO: 11) |
| LCDR1 | KSSQSLLNSGNQKNYLA (SEQ ID NO: 12) |
| LCDR2 | GASTRAS (SEQ ID NO: 13) |
| LCDR3 | QNDLYYPLT (SEQ ID NO: 14) |
| mAb1902 | |
| HCDR1 | SYWMH (SEQ ID NO: 15) |
| HCDR2 | MIHPNSGSTNYNEKFKGR (SEQ ID NO: 16) |
| HCDR3 | LKTGNSFDY (SEQ ID NO: 17) |
| LCDR1 | KSSQSLLNSGNQKNYLT (SEQ ID NO: 18) |

TABLE 4-continued

CDR sequences of murine antibodies

| Antibody | |
|---|---|
| LCDR2 | WASTRES (SEQ ID NO: 19) |
| LCDR3 | QNAYTYPFT (SEQ ID NO: 20) |

2. Selection of Human Germline FR Region Sequences

On the basis of the obtained typical structure of murine antibody VH/VLCDRs, the heavy and light chain variable region sequences were compared with the antibody Germline database to obtain a human germline template with high homology. The human germline light chain framework region was derived from the human kappa light chain gene.

2.1 Humanization and Back Mutation Design of mAb1901

An appropriate human antibody germline was selected for the humanization of mAb1901 murine antibody. The CDR regions of the murine antibody mAb1901 were grafted to the selected humanization template to obtain the humanized variable regions. The humanized heavy chain variable region sequence as shown in SEQ ID NO: 24 and the light chain variable region sequence as shown in SEQ ID NO: 21 were combined with IgG constant regions to form an intact antibody. At the same time, the FR region in the V region of the humanized antibody was subjected to back-mutation, and exemplary back-mutations and combinations are as follows:

TABLE 5

Humanized mAb1901 antibody and back mutations *

| mAb1901 humanized antibody light chain variable region | | mAb1901 humanized antibody heavy chain variable region | |
|---|---|---|---|
| VL1 | no | VH1 | no |
| VL2 | N22S | VH2 | N82T |
| VL3 | N22S, V85I, Y87H | VH3 | V48I, N82T |
| | | VH4 | I69M, N82T |

* All the amino acid positions in the table are numbered according to the Kabat numbering criteria. In case of N82T of the heavy chain variable region, 82 refers to position 82A according to Kabat criteria.

TABLE 6 mAb1901 humanized antibody light chain variable region and heavy chain variable region sequence

| Variable region name (SEQ ID NO:) | sequence |
|---|---|
| VL1 (SEQ ID NO: 21) | DIVMTQSPDSLAVSLGERATINCKSSQSLLNS GNQKNYLAWYQQKPGQPPKLLIYGASTRASGV PDRFSGSGSGTDFTLTISSLQAEDVAVYYCQN DLYYPLTFGQGTKLEIK |
| VL2 (SEQ ID NO: 22) | DIVMTQSPDSLAVSLGERATISCKSSQSLLNS GNQKNYLAWYQQKPGQPPKLLIYGASTRASGV PDRFSGSGSGTDFTLTISSLQAEDVAVYYCQN DLYYPLTFGQGTKLEIK |
| VL3 (SEQ ID NO: 23) | DIVMTQSPDSLAVSLGERATISCKSSQSLLNS GNQKNYLAWYQQKPGQPPKLLIYGASTRASGV PDRFSGSGSGTDFTLTISSLQAEDVAIYHCQN DLYYPLTFGQGTKLEIK |

TABLE 6-continued mAb1901 humanized antibody light chain variable region and heavy chain variable region sequence

| Variable region name (SEQ ID NO:) | sequence |
|---|---|
| VH1 (SEQ ID NO: 24) | EVQLVESGGGLVQPGGSLRLSCAASGFTFSDY GIHWVRQAPGKGLEWVAYISRGSSTIYYADTV KGRFTISRDNAKNSLYLQMNSLRAEDTAVYYC ARGGYDTRNAMDYWGQGTTVTVSS |
| VH2 (SEQ ID NO: 25) | EVQLVESGGGLVQPGGSLRLSCAASGFTFSDY GIHWVRQAPGKGLEWVAYISRGSSTIYYADTV KGRFTISRDNAKNSLYLQMTSLRAEDTAVYYC ARGGYDTRNAMDYWGQGTTVTVSS |
| VH3 (SEQ ID NO: 26) | EVQLVESGGGLVQPGGSLRLSCAASGFTFSDY GIHWVRQAPGKGLEWIAYISRGSSTIYYADTV KGRFTISRDNAKNSLYLQMTSLRAEDTAVYYC ARGGYDTRNAMDYWGQGTTVTVSS |
| VH4 (SEQ ID NO: 27) | EVQLVESGGGLVQPGGSLRLSCAASGFTFSDY GIHWVRQAPGKGLEWVAYISRGSSTIYYADTV KGRFTMSRDNAKNSLYLQMTSLRAEDTAVYYC ARGGYDTRNAMDYWGQGTTVTVSS |

The corresponding heavy chain variable region indicated in the above table can be linked to the human IgG1 heavy chain constant region as shown in SEQ ID NO: 7 to form the heavy chain of a full-length antibody, and the light chain variable region can be linked to the human κ light chain constant region as shown in SEQ ID NO: 8 to form the light chain of a full-length antibody. In other embodiments, the heavy chain variable region and the light chain variable region can also be separately linked to other heavy chain constant region and light chain constant region to form a full-length antibody.

2.2 Humanization and Back Mutation Design of mAb1902

An appropriate human antibody germline was selected for the humanization of mAb1902 murine antibody. The CDR regions of the murine antibody mAb1902 were grafted to the selected humanization template to obtain the humanized variable regions. The humanized heavy chain variable region sequence is as shown in SEQ ID NO: 31 and the light chain variable region sequence is as shown in SEQ ID NO:28; and then recombined with the IgG constant regions to form an intact antibody. At the same time, the FR region in the V region of the humanized antibody was subjected to back-mutation, and exemplary back-mutation methods and combinations are as follows:

TABLE 7

Humanized mAb1902 antibody and back mutation design thereof *

| mAb1902 humanized antibody light chain variable region | | mAb1902 humanized antibody heavy chain variable region | |
|---|---|---|---|
| VL11 | no | VH11 | no |
| VL12 | M4L | VH12 | I69L, R71L, T73K |
| VL13 | M4L, N22S | VH13 | M48I, R66K, V67A, I69L, R71L, T73K |
| | | VH14 | R38K, A40R, M48I, R66K, V67A, I69L, R71L, T73K |

* All the amino acid positions in the table are numbered according to the Kabat numbering criteria.

TABLE 8 mAb1902 humanized antibody light chain variable region and heavy chain variable region sequence

| Variable region name (SEQ ID NO:) | sequence |
|---|---|
| VL11 (SEQ ID NO: 28) | DIVMTQSPDSLAVSLGERATINCKSSQSLLNS GNQKNYLTWYQQKPGQPPKLLIYWASTRESGV PDRFSGSGSGTDFTLTISSLQAEDVAVYYCQN AYTYPFTFGQGTKLEIK |
| VL12 (SEQ ID NO: 29) | DIVLTQSPDSLAVSLGERATINCKSSQSLLNS GNQKNYLTWYQQKPGQPPKLLIYWASTRESGV PDRFSGSGSGTDFTLTISSLQAEDVAVYYCQN AYTYPFTFGQGTKLEIK |
| VL13 (SEQ ID NO: 30) | DIVLTQSPDSLAVSLGERATISCKSSQSLLNS GNQKNYLTWYQQKPGQPPKLLIYWASTRESGV PDRFSGSGSGTDFTLTISSLQAEDVAVYYCQN AYTYPFTFGQGTKLEIK |
| VH11 (SEQ ID NO: 31) | EVQLVQSGAEVKKPGASVKVSCKASGYTFTSY WMHWVRQAPGQRLEWMGMIHPNSGSTNYNEKF KGRVTITRDTSASTAYMELSSLRSEDTAVYYC ARLKTGNSFDYWGQGTTVTVSS |
| VH12 (SEQ ID NO: 32) | EVQLVQSGAEVKKPGASVKVSCKASGYTFTSY WMHWVRQAPGQRLEWMGMIHPNSGSTNYNEKF KGRVTLTLDKSASTAYMELSSLRSEDTAVYYC ARLKTGNSFDYWGQGTTVTVSS |
| VH13 (SEQ ID NO: 33) | EVQLVQSGAEVKKPGASVKVSCKASGYTFTSY WMHWVRQAPGQRLEWIGMIHPNSGSTNYNEKF KGKATLTLDKSASTAYMELSSLRSEDTAVYYC ARLKTGNSFDYWGQGTTVTVSS |
| VH14 (SEQ ID NO: 34) | EVQLVQSGAEVKKPGASVKVSCKASGYTFTSY WMHWVKQRPGQRLEWIGMIHPNSGSTNYNEKF KGKATLTLDKSASTAYMELSSLRSEDTAVYYC ARLKTGNSFDYWGQGTTVTVSS |

The corresponding heavy chain variable region indicated in the above table can be linked to the human IgG1 heavy chain constant region as shown in SEQ ID NO: 7 to form the heavy chain of a full-length antibody, and the light chain variable region can be linked to the human κ light chain constant region as shown in SEQ ID NO: 8 to form the light chain of a full-length antibody.

An example, the antibody full-length sequence is as follows:

chimeric antibody ch1901:
ch1901 heavy chain:
(SEQ ID NO: 35)
EVQLMESGGGLVKPGGSLKLSCAASGFTFSDYGIHWVRQAPEMGLEW

IAYISRGSSTIYYADTVKGRFTMSRDNAKNTLFLQMTSLRSEDTAMY

YCARGGYDTRNAMDYWGQGTSVTVSSASTKGPSVFPLAPSSKSTSGG

TAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNK

ALPAPIEKTISKAKGQPREPQVYTLPPSRDELTKNQVSLTCLVKGFY

PSDIAVEWESNGQPENNYKTTPPVLDSDGSFFLYSKLTVDKSRWQQG

NVFSCSVMHEALHNHYTQKSLSLSPGK;

ch1901 light chain
(SEQ ID NO: 36)
DIVMTQSPSSLSVSAGEKVTMSCKSSQSLLNSGNQKNYLAWYQQKPG

QPPKLLIYGASTRASGVPDRFTGSGSGTDFTLTISSVQAEDLAIYHC

QNDLYYPLTFGAGTKLELKRTVAAPSVFIFPPSDEQLKSGTASVVCL

LNNFYPREAKVQWKVDNALQSGNSQESVTEQDSKDSTYSLSSTLTLS

KADYEKHKVYACEVTHQGLSSPVTKSFNRGEC;

chimeric antibody ch1902:
ch1902 heavy chain
(SEQ ID NO: 37)
EVQLQESGAELVKPGASVKLSCKASGYIFTSYWMHWVKQRPGQGLEW

IGMIHPNSGSTNYNEKFKGKATLTLDKSSSTAYMQLSSLPSEDSAVY

YCARLKTGNSFDYWGQGTTLTVSSASTKGPSVFPLAPSSKSTSGGTA

ALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKAL

PAPIEKTISKAKGQPREPQVYTLPPSRDELTKNQVSLTCLVKGFYPS

DIAVEWESNGQPENNYKTTPPVLDSDGSFFLYSKLTVDKSRWQQGNV

FSCSVMHEALHNHYTQKSLSLSPGK;

ch1902 light chain
(SEQ ID NO: 38)
DIVLTQSPSSLTVTAGEKVTMSCKSSQSLLNSGNQKNYLTWYQQKPG

QPPKLLIYWASTRESGVPDRFTGSGSGTDFTLTISSVQAEDLAIYYC

QNAYTYPFTFGSGTKLEIKRTVAAPSVFIFPPSDEQLKSGTASVVCL

LNNFYPREAKVQWKVDNALQSGNSQESVTEQDSKDSTYSLSSTLTLS

KADYEKHKVYACEVTHQGLSSPVTKSFNRGEC.

TABLE 9

Humanized mAb1901 antibody

| Light chain | Heavy chain | | | |
|---|---|---|---|---|
| | H1 | H2 | H3 | H4 |
| L1 | h1901-1 | h1901-2 | h1901-3 | h1901-4 |
| L2 | h1901-5 | h1901-6 | h1901-7 | h1901-8 |
| L3 | h1901-9 | h1901-10 | h1901-11 | h1901-12 |

The light and heavy chain sequences of the full-length antibody are as follows:

TABLE 10 mAb1901 humanized antibody light chain and heavy chain sequences

| Light chain/heavy chain name (SEQ ID NO:) | sequence |
|---|---|
| L1 (SEQ ID NO: 39) | DIVMTQSPDSLAVSLGERATINCKSSQSLL NSGNQKNYLAWYQQKPGQPPKLLIYGASTR ASGVPDRFSGSGSGTDFTLTISSLQAEDVA VYYCQNDLYYPLTFGQGTKLEIKRTVAAPS |

TABLE 10-continued mAb1901 humanized antibody light chain and heavy chain sequences

| Light chain/heavy chain name (SEQ ID NO:) | sequence |
|---|---|
|  | VFIPPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| L2 (SEQ ID NO: 40) | DIVMTQSPDSLAVSLGERATISCKSSQSLL NSGNQKNYLAWYQQKPGQPPKLLIYGASTR ASGVPDRFSGSGSGTDFTLTISSLQAEDVA VYYCQNDLYYPLTFGQGTKLEIKRTVAAPS VFIPPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| L3 (SEQ ID NO: 41) | DIVMTQSPDSLAVSLGERATISCKSSQSLL NSGNQKNYLAWYQQKPGQPPKLLIYGASTR ASGVPDRFSGSGSGTDFTLTISSLQAEDVA IYHCQNDLYYPLTFGQGTKLEIKRTVAAPS VFIPPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| H1 (SEQ ID NO: 42) | EVQLVESGGGLVQPGGSLRLSCAASGFTFS DYGIHWVRQAPGKGLEWVAYISRGSSTIYY ADTVKGRFTISRDNAKNSLYLQMNSLRAED TAVYYCARGGYDTRNAMDYWGQGTTVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| H2 (SEQ ID NO: 43) | EVQLVESGGGLVQPGGSLRLSCAASGFTFS DYGIHWVRQAPGKGLEWVAYISRGSSTIYY ADTVKGRFTISRDNAKNSLYLQMTSLRAED TAVYYCARGGYDTRNAMDYWGQGTTVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| H3 (SEQ ID NO: 44) | EVQLVESGGGLVQPGGSLRLSCAASGFTFS DYGIHWVRQAPGKGLEWIAYISRGSSTIYY ADTVKGRFTISRDNAKNSLYLQMTSLRAED TAVYYCARGGYDTRNAMDYWGQGTTVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| H4 (SEQ ID NO: 45) | EVQLVESGGGLVQPGGSLRLSCAASGFTFS DYGIHWVRQAPGKGLEWVAYISRGSSTIYY ADTVKGRFTMSRDNAKNSLYLQMTSLRAED TAVYYCARGGYDTRNAMDYWGQGTTVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |

TABLE 11

Humanized mAb1902 antibody

| light chain | Heavy chain | | | |
|---|---|---|---|---|
|  | H11 | H12 | H13 | H14 |
| L11 | h1902-1 | h1902-2 | h1902-3 | h1902-4 |
| L12 | h1902-5 | h1902-6 | h1902-7 | h1902-8 |
| L13 | h1902-9 | h1902-10 | h1902-11 | h1902-12 |

The light and heavy chain sequences of the full-length antibody are as follows:

TABLE 12 mAb1901 humanized antibody light chain and heavy chain sequences

| Light chain/heavy chain name (SEQ ID NO:) | sequence |
|---|---|
| L11 (SEQ ID NO: 46) | DIVMTQSPDSLAVSLGERATINCKSSQSLL NSGNQKNYLTWYQQKPGQPPKLLIYWASTR ESGVPDRFSGSGSGTDFTLTISSLQAEDVA VYYCQNAYTYPFTFGQGTKLEIKRTVAAPS VFIPPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| L12 (SEQ ID NO: 47) | DIVLTQSPDSLAVSLGERATINCKSSQSLL NSGNQKNYLTWYQQKPGQPPKLLIYWASTR ESGVPDRFSGSGSGTDFTLTISSLQAEDVA VYYCQNAYTYPFTFGQGTKLEIKRTVAAPS VFIPPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |
| L13 (SEQ ID NO: 48) | DIVLTQSPDSLAVSLGERATISCKSSQSLL NSGNQKNYLTWYQQKPGQPPKLLIYWASTR ESGVPDRFSGSGSGTDFTLTISSLQAEDVA VYYCQNAYTYPFTFGQGTKLEIKRTVAAPS VFIPPPSDEQLKSGTASVVCLLNNFYPREA KVQWKVDNALQSGNSQESVTEQDSKDSTYS LSSTLTLSKADYEKHKVYACEVTHQGLSSP VTKSFNRGEC |

TABLE 12-continued mAb1901 humanized antibody light chain and heavy chain sequences

| Light chain/heavy chain name (SEQ ID NO:) | sequence |
|---|---|
| H11 (SEQ ID NO: 49) | EVQLVQSGAEVKKPGASVKVSCKASGYTFT SYWMHWVRQAPGQRLEWMGMIHPNSGSTNY NEKFKGRVTITRDTSASTAYMELSSLRSED TAVYYCARLKTGNSFDYWGQGTTVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSRDELT KNQVSLTCLVKGFYPSDIAVEWESNGQPEN NYKTTPPVLDSDGSFFLYSKLTVDKSRWQQ GNVFSCSVMHEALHNHYTQKSLSLSPGK |
| H12 (SEQ ID NO: 50) | EVQLVQSGAEVKKPGASVKVSCKASGYTFT SYWMHWVRQAPGQRLEWMGMIHPNSGSTNY NEKFKGRVTLTLDKSASTAYMELSSLRSED TAVYYCARLKTGNSFDYWGQGTTVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLEPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSRDELT KNQVSLTCLVKGFYPSDIAVEWESNGQPEN NYKTTPPVLDSDGSFFLYSKLTVDKSRWQQ GNVFSCSVMHEALHNHYTQKSLSLSPGK |
| H13 (SEQ ID NO: 51) | EVQLVQSGAEVKKPGASVKVSCKASGYTFT SYWMHWVRQAPGQRLEWIGMIHPNSGSTNY NEKFKGKATLTLDKSASTAYMELSSLRSED TAVYYCARLKTGNSFDYWGQGTTVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSRDELT KNQVSLTCLVKGFYPSDIAVEWESNGQPEN NYKTTPPVLDSDGSFFLYSKLTVDKSRWQQ GNVFSCSVMHEALHNHYTQKSLSLSPGK |
| H14 (SEQ ID NO: 52) | EVQLVQSGAEVKKPGASVKVSCKASGYTFT SYWMHWVKQRPGQRLEWIGMIHPNSGSTNY NEKFKGKATLTLDKSASTAYMELSSLRSED TAVYYCARLKTGNSFDYWGQGTTVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLEPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSRDELT KNQVSLTCLVKGFYPSDIAVEWESNGQPEN NYKTTPPVLDSDGSFFLYSKLTVDKSRWQQ GNVFSCSVMHEALHNHYTQKSLSLSPGK |

The positive control antibody of the present disclosure was IMAB-362 (available from WO2016166122):

```
IMAB-362 heavy chain
                                        (SEQ ID NO: 53)
  1    QVQLQQPGAE LVRPGASVKL SCKASGYTFT SYWINWVKQR PGQGLEWIGN

51    IYPSDSYTNY NQKFKDKATL TVDKSSSTAY MQLSSPTSED SAVYYCTRSW

101    RGNSFDYWGQ GTTLTVSSAS TKGPSVFPLA PSSKSTSGGT AALGCLVKDY

151    FPEPVTVSWN SGALTSGVHT FPAVLQSSGL YSLSSVVTVP SSSLGTQTYI

201    CNVNHKPSNT KVDKRVEPKS CDKTHTCPPC PAPELLGGPS VFLFPPKPKD

251    TLMISRTPEV TCVVVDVSHE DPEVKFNWYV DGVEVHNAKT KPREEQYNST

301    YRVVSVLTVL HQDWLNGKEY KCKVSNKALP APIEKTISKA KGQPREPQVY

351    TLPPSREEMT KNQVSLTCLV KGFYPSDIAV EWESNGQPEN NYKTTPPVLD

401    SDGSFFLYSK LTVDKSRWQQ GNVFSCSVMH EALHNHYTQK SLSLSPGK.

IMAB-362 light chain
                                        (SEQ ID NO: 54)
  1    DIVMTQSPSS LTVTAGEKVT MSCKSSQSLL NSGNQKNYLT WYQQKPGQPP

51    KLLIYWASTR ESGVPDRFTG SGSGTDFTLT ISSVQAEDLA VYYCQNDYSY

101    PFTFGSGTKL EIKRTVAAPS VFIFPPSDEQ LKSGTASVVC LLNNFYPREA

151    KVQWKVDNAL QSGNSQESVT EQDSKDSTYS LSSTLTLSKA DYEKHKVYAC

201    EVTHQGLSSP VTKSFNRGEC.
```

The above-mentioned antibodies were cloned, expressed and purified by conventional gene cloning and recombinant expression methods.

In Vitro Biological Evaluation

Test Example 1: ELISA Binding Assay at the Cellular Level

Cell-based ELISA assay was used to detect the binding property of the Claudin 18.2 antibodies. The NUGC4 cells stably expressing Claudin 18.2 were cultured in a 96-well cell plate (Corning, 3599), until the cell growth density reached 90%, 4% paraformaldehyde was added to fix the cells for 1 hour. The plate was washed with PBST buffer (PBS containing 0.05% Tween-20, pH 7.4) for 3 times, and was then blocked by adding 200 μl/well of 5% skimmed milk (Bright skimmed milk powder) diluted with PBS as a blocking solution, and incubated in a 37° C. incubator for 2.5 hours or 4° C. overnight (16-18 hours). After blocking, the blocking solution was discarded and the plate was washed 3 times with PBST buffer, 50 μl/well of the test antibodies diluted with sample diluent (PBS containing 1% skimmed milk, pH7.4) were added, and placed in a 37° C. incubate for 2 hours. After the incubation was finished, the plate was washed for 5 times with PBST, 100 μl/well of HRP-labeled goat anti-human secondary antibody (Jackson Immuno Research, Cat No. 109-035-003) diluted with sample diluent was added, and incubated at 37° C. for 1 hour. After the plate was washed for 6 times with PBST, 50 μl/well of TMB chromogenic substrate (KPL, Cat No. 52-00-03) was added, incubated at room temperature for 10-15 min, and 50 μl/well of 1M $H_2SO_4$ was added to stop the reaction. The absorbance value was read with MD Versa Max™ microplate reader at 450 nm, and the EC50 value showing the Claudin18.2 antibody binding to Claudin18.2 was calculated (The results are shown in the table below).

TABLE 13

| Binding activity of antibody | | | |
|---|---|---|---|
| Antibody | IMAB362 | ch1901 | ch1902 |
| Emax | 1.175 | 1.399 | 1.272 |
| EC50 (nM) | 0.108 | 0.098 | 0.074 |

TABLE 14-1

| Binding activity of mAb1901 humanized antibody | | |
|---|---|---|
| Antibody | Emax | EC50 (nM) |
| IMAB362 | 1.115 | 0.086 |
| h1901-2 | 1.039 | 0.076 |
| h1901-3 | 1.1055 | 0.22 |
| h1901-4 | 0.986 | 0.201 |
| h1901-6 | 0.937 | 0.091 |
| h1901-7 | 0.921 | 0.166 |
| h1901-8 | 1.047 | 0.091 |
| h1901-11 | 1.44 | 0.076 |
| h1901-12 | 1.22 | 0.116 |

TABLE 14-2

| Binding activity of mAb1902 humanized antibody | | |
|---|---|---|
| Antibody | Emax | EC50 (nM) |
| IMAB362 | 0.88 | 0.187 |
| h1902-1 | 0.87 | 0.113 |
| h1902-2 | 0.88 | 0.107 |

TABLE 14-2-continued

| Binding activity of mAb1902 humanized antibody | | |
|---|---|---|
| Antibody | Emax | EC50 (nM) |
| h1902-3 | 0.84 | 0.175 |
| h1902-4 | 0.82 | 0.087 |
| h1902-5 | 0.9 | 0.098 |
| h1902-6 | 0.78 | 0.141 |
| h1902-7 | 0.75 | 0.121 |
| h1902-8 | 0.89 | 0.132 |
| h1902-9 | 0.75 | 0.137 |
| h1902-10 | 0.89 | 0.133 |

Test Example 2: Binding Assay of Antibodies at the Cellular Level $1 \times 10^6$/ml cell suspension was prepared with the NUGC4 cells stably expressing Claudin 18.2 and FACS buffer (2% Fetal Bovine Serum (Gibco, 10099141) in PBS (Sigma, P4417-100TAB), pH7.4), and was added into a 96-well round bottom plate (Corning, 3795) at 100 μl/well. After centrifugation to remove the supernatant, various concentrations of the test Claudin 18.2 antibodies diluted with FACS buffer were added at 50 μl/well, and incubated for 1 hour in a 4° C. refrigerator in the dark. After centrifugation and washing with FACS buffer at 300 g for 3 times, the working concentration of Alexa Fluor 488-coated anti-human IgG (H+L) (invitrogen, A-11013) was added and incubated in a 4° C. refrigerator in the dark for 40 minutes. After centrifugation and washing with FACS buffer at 300 g for 3 times, the geometric mean fluorescence intensity was measured on BD FACS CantoII flow cytometer, and EC50 value showing Claudin 18.2 antibody binding to NUGC4 cells stably expressing Claudin 18.2 was calculated. The results are shown in FIG. 1.

Test Example 3: Endocytosis Assay of Antibodies

Figure 2:
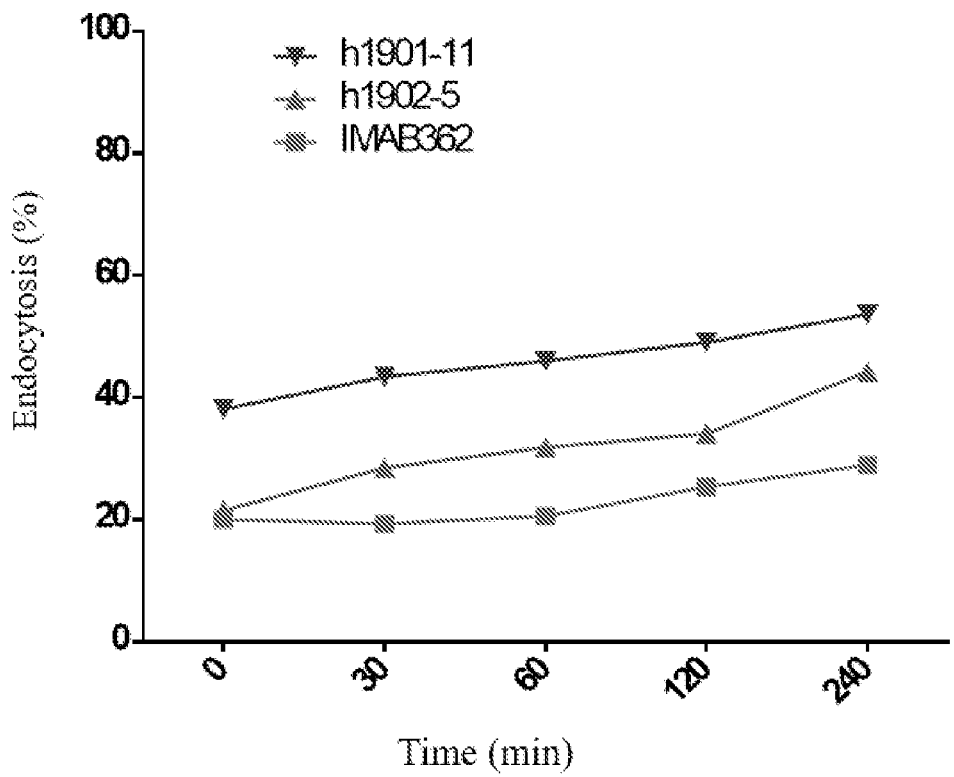
FIG. 2: endocytosis assay of humanized antibodies in NUGC4 cells.

The test Claudin 18.2 antibody pre-labeled with DyLight 488 NHS Ester (thermofisher, 46403) was added into $1 \times 10^6$/ml NUGC4 cells stably expressing Claudin 18.2 at a final concentration of 5 μg/ml, and placed on ice for 1 hour-incubation in the dark, centrifuged and washed 3 times with pre-cooled FACS buffer (2% fetal calf serum in PBS, pH 7.4), after the supernatant was removed, pre-warmed complete medium was added, and placed in a cell incubator at 37° C., 5% $CO_2$. The cells were taken out after 0, 0.5, 1, 2, and 4 hours respectively, and placed on ice in the dark. After all the samples were collected, centrifuged at 300 g at low temperature, elution buffer (0.05M glycine, 0.1M sodium chloride, pH1.7) was added and incubated at room temperature for 7 minutes. The samples were centrifuged and washed with FACS buffer at 300 g for once, the geometric mean fluorescence intensity was measured on BD FACS CantoII flow cytometer, and the endocytosis efficiency of Claudin 18.2 antibody for NUGC4 cells stably expressing Claudin 18.2 was calculated. The results show (see FIG. 2) that the humanized antibodies have favorable endocytosis efficiency.

Test Example 4: Determination of Antibody Affinity Based on Flow Cytometry

On the day of testing, HEK293/hClaudin18.2 cells were collected in a U-bottom 96-well plate, with $1 \times 10^5$ to $2 \times 10^5$ cells per well. The Claudin 18.2 antibody was added, with an initial concentration of 5 µg/ml, 2× gradient dilutions (12 concentration points), and incubate at 4° C. for 1 hour. The positive control was IMAB362, and the well without antibody was set as negative control. The antibody was removed by centrifugation, and then 100 µl/well of FITC anti-human IgG Fc antibody (200×) was added, incubated at 4° C. for 30 minutes in the dark, washed twice with PBS+2% FBS, and prepared for flow cytometry detection. The BD FACS CantoII was started and preheated, a new assay was established by BD FACSDiva software. The HEK293/hClaudin18.2 negative control sample was detected, and the FSC and SSC voltages were adjusted to appropriate values and saved. The blank sample B and standard curve 1 were detected respectively according to the instructions of Quantum™ FITC-5 MESF Kit. The FITC voltage was adjusted to an appropriate value and saved. The samples in the U-bottom 96-well plate were detected under the saved voltage, and the data were recorded. Flowjo software was used to analyze the experimental data to obtain the Geo Mean value, and the MESF-Geo Mean standard curve was fitted according to the instructions of Quantum™ FITC-5 MESF Kit. The molar concentrations of the Claudin18.2 antibody binding to HEK293/hClaudin18.2 cells and concentrations of the free antibody were calculated based on the concentration fluorescence value of FITC anti-human IgG Fc antibody, and the Bmax and dissociation constant KD of the antibody were calculated by using Scatchard plotting method. The results are shown in Table 15.

TABLE 15

Affinity of humanized antibody at the cellular level

| Antibody | IMAB362 | h1901-11 | h1902-5 |
|---|---|---|---|
| KD (nM) | 10.2 | 6.8 | 1.64 |

Test Example 5: Evaluation of ADCC Effect of Antibody

Various NUGC4 cells (high, medium and low expression of Claudin 18.2) were digested, centrifuged at 1000 rpm, and resuspended for counting. The cells were re-suspended in phenol red-free RPMI 1640 (Gibco, CAT #11835-030) containing 10% FBS (New Zealand Ultra-low IgG Fetal Bovine Serum, Gibco, 1921005PJ) at $3\times10^5$ cells/ml. 25 µl of cells were added to each well of a 96-well plate (Corning, 3903), 7500 cells/well. The antibody was diluted in the above-mentioned phenol red-free medium to prepare a 3× antibody dilution solution, and 25 µl/well of antibody was added to the cell plate and incubated in a 37° C., 5% $CO_2$ incubator for 0.5 hours.

The effector cells (FcrR3A-V158-NFAT-RE-Jurkat cells) were collected, centrifuged at 1000 rpm, and resuspended for counting. The cells were re-suspended in phenol red-free RPMI 1640 containing 10% FBS (New Zealand Ultra-low IgG Fetal Bovine Serum) at $3\times10^6$ cells/ml, and 25 µl of cells were added to the assay plate ($7.5\times10^4$ cells/well) and incubated in a 37° C., 5% $CO_2$ incubator for 6 hours.

75 µl/well of Bright-Glo (Promega, E2610) was added to each well of the assay plate, and the chemiluminescence was detected with a microplate reader (PerkinElmer, VITOR3).

Figure 3A:
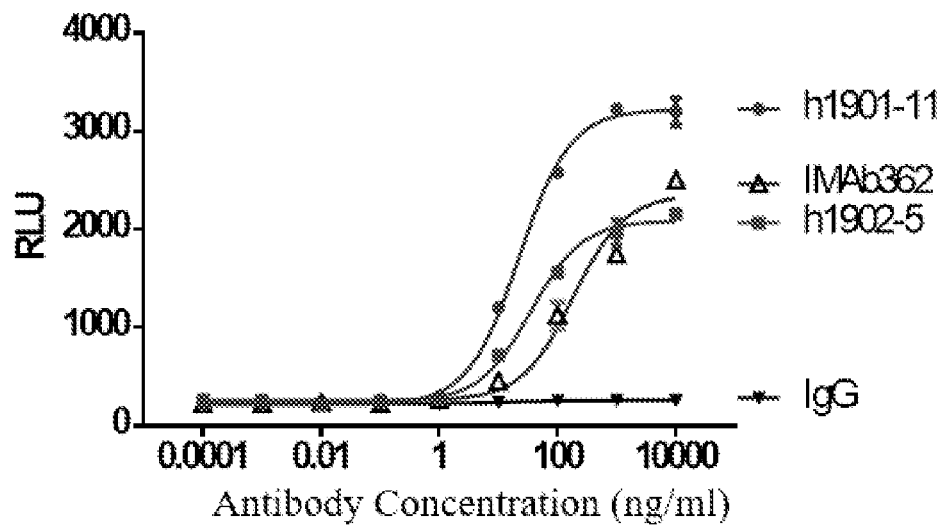
FIG. 3A to FIG. 3C: detection of ADCC effect of antibodies in NUGC4 cells with different expression levels of Claudin 18.2.
Figure 3B:
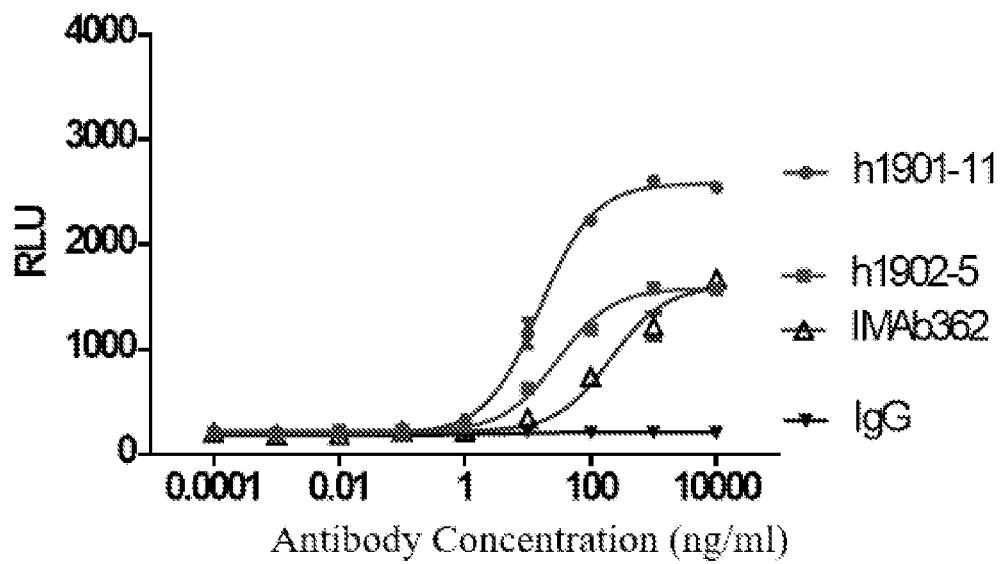
Figure 3C:
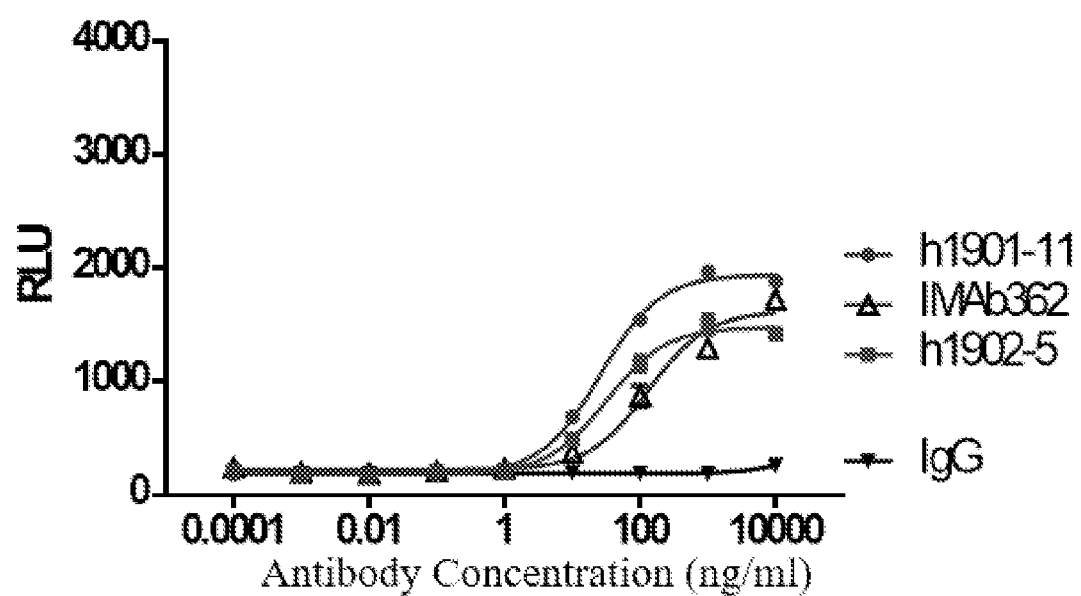

The results show (see Table 16 and FIG. 3A-FIG. 3C) that both antibody h1901-11 and h1902-5 show very strong ADCC activity in NUGC4 cells expressing low, medium and high levels of Claudin 18.2.

TABLE 16

ADCC effects of antibodies in NUGC4 cells with different expression levels of Claudin 18.2

| Expression level of Claudin 18.2 in NUGC4 | | h1901-11 | h1902-5 | IMAB362 |
|---|---|---|---|---|
| Low expression | IC50 (ng/ml) | 22.42 | 35.46 | 183.4 |
| Medium expression | IC50 (ng/ml) | 15.35 | 30.00 | 210.4 |
| High expression | IC50 (ng/ml) | 26.17 | 32.16 | 132.6 |

What is claimed is:

1. An anti-Claudin 18.2 antibody comprising a heavy chain variable region and a light chain variable region, wherein:
   i) the heavy chain variable region comprises HCDR1, HCDR2 and HCDR3 as shown in SEQ ID NO: 15, SEQ ID NO: 16 and SEQ ID NO: 17, respectively, and the light chain variable region comprises LCDR1, LCDR2 and LCDR3 as shown in SEQ ID NO: 18, SEQ ID NO: 19 and SEQ ID NO: 20, respectively; or
   ii) the heavy chain variable region comprises HCDR1, HCDR2 and HCDR3 as shown in SEQ ID NO: 9, SEQ ID NO: 10 and SEQ ID NO: 11, respectively, and the light chain variable region comprises LCDR1, LCDR2 and LCDR3 as shown in SEQ ID NO: 12, SEQ ID NO: 13 and SEQ ID NO: 14, respectively.

2. The anti-Claudin 18.2 antibody according to claim 1, wherein the antibody is a murine antibody, a chimeric antibody, or a humanized antibody.

3. The anti-Claudin 18.2 antibody according to claim 1, comprising a heavy chain variable region and a light chain variable region, wherein:
   1) The amino acid sequence of the heavy chain variable region is as shown in SEQ ID NO: 3 or has at least 90% identity to SEQ ID NO: 3, and the amino acid sequence of the light chain variable region is as shown in SEQ ID NO: 4 or has at least 90% identity to SEQ ID NO: 4;
   2) The amino acid sequence of the heavy chain variable region is as shown in SEQ ID NO: 24 or has at least 90% identity to SEQ ID NO: 24, and the amino acid sequence of the light chain variable region is as shown in SEQ ID NO: 21 or has at least 90% identity to SEQ ID NO: 21;
   3) The amino acid sequence of the heavy chain variable region is as shown in SEQ ID NO: 5 or has at least 90% identity to SEQ ID NO: 5, and the amino acid sequence of the light chain variable region is as shown in SEQ ID NO: 6 or has at least 90% identity to SEQ ID NO: 6; or
   4) The amino acid sequence of the heavy chain variable region is as shown in SEQ ID NO: 31 or has at least 90% identity to SEQ ID NO: 31, and the amino acid sequence of the light chain variable region is as shown in SEQ ID NO: 28 or has at least 90% identity to SEQ ID NO: 28.

4. The anti-Claudin 18.2 antibody according to claim 3, wherein the antibody is a humanized antibody comprising a framework region derived from a human antibody or a framework region variant thereof, and the framework region variant has 1 to 10 back mutation(s) on the human antibody light chain framework region and/or the heavy chain framework region;
   wherein the framework region variant comprises mutation(s) selected from a) or b) below:
   a) one or more back mutation(s) selected from the group consisting of 22S, 85I and 87H comprised in the light chain variable region, and/or one or more back mutation(s) selected from the group consisting of 48I, 82T and 69M comprised in the heavy chain variable region; or
   b) one or more back mutation(s) selected from the group consisting of 4L and 22S comprised in the light chain variable region, and/or one or more back mutation(s) selected from the group consisting of 38K, 40R, 48I, 66K, 67A, 69L, 71L and 73K comprised in the heavy chain variable region.

5. The anti-Claudin 18.2 antibody according to claim 2, wherein the antibody comprises a heavy chain variable region and a light chain variable region as shown below:
   i) the heavy chain variable region sequence as shown in SEQ ID NO: 3 and the light chain variable region sequence as shown in SEQ ID NO: 4; or
   ii) the heavy chain variable region sequence as shown in SEQ ID NO: 24, 25, 26 or 27 and the light chain variable region sequence as shown in SEQ ID NO: 21, 22 or 23; or
   iii) the heavy chain variable region sequence as shown in SEQ ID NO: 5 and the light chain variable region sequence as shown in SEQ ID NO: 6; or
   iv) the heavy chain variable region sequence as shown in SEQ ID NO: 31, 32, 33 or 34 and the light chain variable region sequence as shown in SEQ ID NO: 28, 29 or 30.

6. The anti-Claudin 18.2 antibody according to claim 1, wherein the antibody further comprises a heavy chain constant region and a light chain constant region;
   wherein the heavy chain constant region is selected from the group consisting of human IgG1, IgG2, IgG3 and IgG4 constant region(s) and variant(s) thereof, and the light chain constant region is selected from the group consisting of human antibody κ and λ chain constant region(s) and variant(s) thereof.

7. The anti-Claudin 18.2 antibody according to claim 1, comprising:
   c) a heavy chain as shown in SEQ ID NO: 35 and a light chain as shown in SEQ ID NO: 36;
   d) a heavy chain as shown in SEQ ID NO: 42, 43, 44 or 45 and a light chain as shown in SEQ ID NO: 39, 40 or 41;
   e) a heavy chain as shown in SEQ ID NO: 37 and a light chain as shown in SEQ ID NO: 38; or
   f) a heavy chain as shown in SEQ ID NO: 49, 50, 51 or 52 and a light chain as shown in SEQ ID NO: 46, 47 or 48.

8. The anti-Claudin 18.2 antibody according to claim 1, comprising:
   a heavy chain as shown in SEQ ID NO: 44 and a light chain as shown in SEQ ID NO: 41; or
   a heavy chain as shown in SEQ ID NO: 49 and a light chain as shown in SEQ ID NO: 47.

9. A nucleic acid molecule encoding the anti-Claudin 18.2 antibody of claim 1.

10. A host cell comprising the nucleic acid molecule of claim 9.

11. An antibody-drug conjugate comprising the anti-Claudin 18.2 antibody according to claim 1 and a cytotoxic drug.

12. A pharmaceutical composition, comprising a therapeutically effective amount of the anti-Claudin 18.2 antibody according to claim 1 and one or more pharmaceutically acceptable carriers, diluents, buffers or excipients.

13. A method for the treatment of a disease associated with Claudin 18.2, the method including administering to a subject a therapeutically effective amount of the anti-Claudin 18.2 antibody of claim 1; wherein the disease is a tumor.

14. The method of claim 13, wherein the disease is selected from the group consisting of: head and neck squamous cell cancer, head and neck cancer, brain cancer, glioma, glioblastoma multiforme, neuroblastoma, central nervous system cancer, neuroendocrine tumor, laryngopharyngeal carcinoma, nasopharyngeal cancer, esophageal cancer, thyroid cancer, malignant pleural mesothelioma, lung cancer, breast cancer, liver cancer, hepatocellular tumor, hepatocellular carcinoma, liver and gallbladder cancer, pancreatic cancer, gastric cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, Krukenberg tumor, myeloproliferative tumor, squamous cell carcer, Ewing sarcoma, systemic light chain amyloidosis and Merkel cell cancer.

15. The anti-Claudin 18.2 antibody according to claim 4, wherein the framework region variant comprises mutation(s) selected from a-1) or b-1) below:
   a-1) amino acid back mutations 22S, 85I and 87H comprised in the light chain variable region, and back mutations 48I and 82T comprised in the heavy chain variable region; or
   b-1) back mutation 4L comprised in the light chain variable region;
back mutation 82T comprised in the heavy chain variable region, wherein "82" indicates position 82A according to Kabat Criteria.

16. The anti-Claudin 18.2 antibody according to claim 5, wherein the anti-Claudin 18.2 antibody or antigen-binding fragment thereof comprises a heavy chain variable region and a light chain variable region as shown below:
   i) the heavy chain variable region sequence as shown in SEQ ID NO: 31 and the light chain variable region sequence as shown in SEQ ID NO: 29; or
   ii) the heavy chain variable region sequence as shown in SEQ ID NO: 26 and the light chain variable region sequence as shown in SEQ ID NO: 23.

17. The anti-Claudin 18.2 antibody according to claim 6, wherein the anti-Claudin 18.2 antibody comprises the heavy chain constant region as shown in SEQ ID NO: 7 and the light chain constant region as shown in SEQ ID NO: 8;
   the anti-Claudin 18.2 antibody comprises a heavy chain having at least 90% identity to SEQ ID NO: 35 or 42, and a light chain having at least 90% identity to SEQ ID NO: 36 or 39; or
   a heavy chain having at least 90% identity to SEQ ID NO: 37 or 49, and a light chain having at least 90% identity to SEQ ID NO: 38 or 46.

* * * * *

SEQUENCE LISTING

<160> NUMBER OF SEQ ID NOS: 54

<210> SEQ ID NO 1
<211> LENGTH: 261
<212> TYPE: PRT
<213> ORGANISM: Homo sapiens
<220> FEATURE:
<221> NAME/KEY: PEPTIDE
<223> OTHER INFORMATION: Claudin18.2 protein

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 3350
<212> TYPE: DNA
<213> ORGANISM: Homo sapiens
<220> FEATURE:
<221> NAME/KEY: gene
<223> OTHER INFORMATION: Claudin18.2

<400> SEQUENCE: 2
agaattgcgc tgtccacttg tcgtgtggct ctgtgtcgac actgtgcgcc accatggccg      60
tgactgcctg tcagggcttg gggttcgtgg tttcactgat gggattgcg ggcatcattg     120
ctgccacctg catggaccag tggagcaccc aagacttgta caacaacccc gtaacagctg     180
ttttcaacta ccaggggctg tggcgctcct gtgtccgaga gagctctggc ttcaccgagt     240
gccggggcta cttcacccct gctgggctgc cagccatgct gcaggcagtg cgagccctga     300
tgatcgtagg catcgtcctg ggtgccattg gcctcctggt atccatcttt gccctgaaat     360
gcatccgcat tggcagcatg gaggactctg ccaaagccaa catgacactg acctccggga     420
tcatgttcat tgtctcaggt ctttgtgcaa ttgctggagt gtctgtgttt gccaacatgc     480
tggtgactaa cttctggatg tccacagcta acatgtacac cggcatgggt gggatggtgc     540
agactgttca gaccaggtac acatttggtg cggctctgtt cgtgggctgg gtcgctggag     600
gcctcacact aattgggggt gtgatgatgt gcatcgcctg ccggggcctg gcaccagaag     660
aaaccaacta caaagccgtt tcttatcatg cctcaggcca cagtgttgcc tacaagcctg     720
gaggcttcaa ggccagcact ggctttgggt ccaacaccaa aacaagaag atatacgatg     780
gaggtgcccg cacagaggac gaggtacaat cttatccttc aagcacgac tatgtgtaat     840
gctctaagac ctctcagcac gggcggaaga aactcccgga gagctcaccc aaaaaacaag     900
gagatcccat ctagatttct tcttgctttt gactcacagc tggaagttag aaaagcctcg     960

```
atttcatctt tggagaggcc aaatggtctt agcctcagtc tctgtctcta aatattccac    1020
cataaaacag ctgagttatt tatgaattag aggctatagc tcacattttc aatcctctat    1080
ttcttttttt aaatataact ttctactctg atgagagaat gtggttttaa tctctctctc    1140
acattttgat gatttagaca gactccccct cttcctccta gtcaataaac ccattgatga    1200
tctatttccc agcttatccc caagaaaact tttgaaagga aagagtagac ccaaagatgt    1260
tattttctgc tgtttgaatt ttgtctcccc accccaact tggctagtaa taaacactta     1320
ctgaagaaga agcaataaga gaaagatatt tgtaatctct ccagcccatg atctcggttt    1380
tcttacactg tgatcttaaa agttaccaaa ccaaagtcat tttcagtttg aggcaaccaa    1440
acctttctac tgctgttgac atcttcttat tacagcaaca ccattctagg agtttcctga   1500
gctctccact ggagtcctct ttctgtcgcg ggtcagaaat tgtccctaga tgaatgagaa    1560
aattattttt tttaatttaa gtcctaaata tagttaaaat aaataatgtt ttagtaaaat    1620
gatacactat ctctgtgaaa tagcctcacc cctacatgtg gatagaagga aatgaaaaaa    1680
taattgcttt gacattgtct atatggtact ttgtaaagtc atgcttaagt acaaattcca    1740
tgaaaagctc actgatccta attctttccc tttgaggtct ctatggctct gattgtacat    1800
gatagtaagt gtaagccatg taaaaagtaa ataatgtctg ggcacagtgg ctcacgcctg    1860
taatcctagc actttgggag gctgaggagg aaggatcact tgagcccaga gttcgagac    1920 tagcctgggc aacatggaga agccctgtct ctacaaaata cagagagaaa aaatcagcca    1980
gtcatggtgg cctacacctg tagtcccagc attccgggag gctgaggtgg gaggatcact    2040
tgagcccagg gaggttgggg ctgcagtgag ccatgatcac accactgcac tccagccagg    2100
tgacatagcg agatcctgtc taaaaaaata aaaaataaat aatggaacac agcaagtcct    2160
aggaagtagg ttaaaactaa ttcttttaaaa aaaaaaaaaa gttgagcctg aattaaatgt    2220
aatgtttcca agtgacaggt atccacattt gcatggttac aagccactgc cagttagcag    2280
tagcactttc ctggcactgt ggtcggtttt gttttgtttt gctttgttta gagacggggt    2340
ctcactttcc aggctggcct caaactcctg cactcaagca attcttctac cctggcctcc    2400
caagtagctg gaattacagg tgtgcgccat cacaactagc tggtggtcag ttttgttact    2460
ctgagagctg ttcacttctc tgaattcacc tagagtggtt ggaccatcag atgtttgggc    2520
aaaactgaaa gctctttgca accacacacc ttccctgagc ttacatcact gccctttga    2580 gcagaaagtc taaattcctt ccaagacagt agaattccat cccagtacca aagccagata    2640
ggccccctag gaaactgagg taagagcagt ctctaaaaac tacccacagc agcattggtg    2700
caggggaact tggccattag gttattattt gagaggaaag tcctcacatc aatagtacat    2760
atgaaagtga cctccaaggg gattggtgaa tactcataag gatcttcagg ctgaacagac    2820
tatgtctggg gaagaacgg attatgcccc attaaataac aagttgtgtt caagagtcag     2880
agcagtgagc tcagaggccc ttctcactga gacagcaaca tttaaaccaa accagaggaa    2940
gtatttgtgg aactcactgc ctcagtttgg gtaaaggatg agcagacaag tcaactaaag    3000
aaaaaagaaa agcaaggagg agggttgagc aatctagagc atggagtttg ttaagtgctc    3060
tctggatttg agttgaagag catccatttg agttgaaggc cacagggcac aatgagctct    3120
cccttctacc accagaaagt ccctggtcag gtctcaggta gtgcggtgtg gctcagctgg    3180 gttttttaatt agcgcattct ctatccaaca tttaattgtt tgaaagcctc catatagtta    3240
gattgtgctt tgtaattttg ttgttgttgc tctatcttat tgtatatgca ttgagtatta    3300
```
acctgaatgt tttgttactt aaatattaaa aacactgtta tcctacagtt           3350

<210> SEQ ID NO 3
<211> LENGTH: 120
<212> TYPE: PRT
<213> ORGANISM: Mus musculus
<220> FEATURE:
<221> NAME/KEY: DOMAIN
<223> OTHER INFORMATION: mAb1901 murine antibody heavy chain variable region

<400> SEQUENCE: 3

Glu Val Gln Leu Met Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Ile His Trp Val Arg Gln Ala Pro Glu Met Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Tyr Asp Thr Arg Asn Ala Met Asp Tyr Trp Gly Gln
            100                 105                 110

Gly Thr Ser Val Thr Val Ser Ser
        115                 120

<210> SEQ ID NO 4
<211> LENGTH: 113
<212> TYPE: PRT
<213> ORGANISM: Mus musculus
<220> FEATURE:
<221> NAME/KEY: DOMAIN
<223> OTHER INFORMATION: mAb1901 murine antibody light chain variable region

<400> SEQUENCE: 4

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr His Cys Gln Asn
                85                  90                  95

Asp Leu Tyr Tyr Pro Leu Thr Phe Gly Ala Gly Thr Lys Leu Glu Leu
            100                 105                 110

Lys

<210> SEQ ID NO 5
<211> LENGTH: 118
<212> TYPE: PRT
<213> ORGANISM: Mus musculus
<220> FEATURE:

```
<221> NAME/KEY: DOMAIN
<223> OTHER INFORMATION: mAb1902 murine antibody heavy chain variable
      region

<400> SEQUENCE: 5

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ser Ser Thr Ala Tyr
65                  70                  75                  80

Met Gln Leu Ser Ser Leu Pro Ser Glu Asp Ser Ala Val Tyr Tyr Cys
                85                  90                  95

Ala Arg Leu Lys Thr Gly Asn Ser Phe Asp Tyr Trp Gly Gln Gly Thr
            100                 105                 110

Thr Leu Thr Val Ser Ser
        115

<210> SEQ ID NO 6
<211> LENGTH: 113
<212> TYPE: PRT
<213> ORGANISM: Mus musculus
<220> FEATURE:
<221> NAME/KEY: DOMAIN
<223> OTHER INFORMATION: mAb1902 murine antibody light chain variable
      region

<400> SEQUENCE: 6

Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Thr Tyr Pro Phe Thr Phe Gly Ser Gly Thr Lys Leu Glu Ile
            100                 105                 110

Lys

<210> SEQ ID NO 7
<211> LENGTH: 330
<212> TYPE: PRT
<213> ORGANISM: Homo sapiens
<220> FEATURE:
<221> NAME/KEY: DOMAIN
<223> OTHER INFORMATION: human IgG1 antibody heavy chain constant region

<400> SEQUENCE: 7

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 107
<212> TYPE: PRT
<213> ORGANISM: Homo sapiens
<220> FEATURE:
<221> NAME/KEY: DOMAIN
<223> OTHER INFORMATION: human antibody kappa light chain constant
      region

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
                35                  40                  45
Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 9
<211> LENGTH: 5
<212> TYPE: PRT
<213> ORGANISM: Artificial Sequence
<220> FEATURE:
<221> NAME/KEY: DOMAIN
<223> OTHER INFORMATION: mAb1901 HCDR1

<400> SEQUENCE: 9

Asp Tyr Gly Ile His
1               5

<210> SEQ ID NO 10
<211> LENGTH: 17
<212> TYPE: PRT
<213> ORGANISM: Artificial Sequence
<220> FEATURE:
<221> NAME/KEY: DOMAIN
<223> OTHER INFORMATION: mAb1901 HCDR2

<400> SEQUENCE: 10

Tyr Ile Ser Arg Gly Ser Ser Thr Ile Tyr Tyr Ala Asp Thr Val Lys
1               5                   10                  15

Gly

<210> SEQ ID NO 11
<211> LENGTH: 11
<212> TYPE: PRT
<213> ORGANISM: Artificial Sequence
<220> FEATURE:
<221> NAME/KEY: DOMAIN
<223> OTHER INFORMATION: mAb1901 HCDR3

<400> SEQUENCE: 11

Gly Gly Tyr Asp Thr Arg Asn Ala Met Asp Tyr
1               5                   10

<210> SEQ ID NO 12
<211> LENGTH: 17
<212> TYPE: PRT
<213> ORGANISM: Artificial Sequence
<220> FEATURE:
<221> NAME/KEY: DOMAIN
<223> OTHER INFORMATION: mAb1901 LCDR1

<400> SEQUENCE: 12

Lys Ser Ser Gln Ser Leu Leu Asn Ser Gly Asn Gln Lys Asn Tyr Leu
1               5                   10                  15

Ala

<210> SEQ ID NO 13
<211> LENGTH: 7
<212> TYPE: PRT
<213> ORGANISM: Artificial Sequence
```

```
<220> FEATURE:
<221> NAME/KEY: DOMAIN
<223> OTHER INFORMATION: mAb1901 LCDR2

<400> SEQUENCE: 13

Gly Ala Ser Thr Arg Ala Ser
1               5

<210> SEQ ID NO 14
<211> LENGTH: 9
<212> TYPE: PRT
<213> ORGANISM: Artificial Sequence
<220> FEATURE:
<221> NAME/KEY: DOMAIN
<223> OTHER INFORMATION: mAb1901 LCDR3

<400> SEQUENCE: 14

Gln Asn Asp Leu Tyr Tyr Pro Leu Thr
1               5

<210> SEQ ID NO 15
<211> LENGTH: 5
<212> TYPE: PRT
<213> ORGANISM: Artificial Sequence
<220> FEATURE:
<221> NAME/KEY: DOMAIN
<223> OTHER INFORMATION: mAb1902 HCDR1

<400> SEQUENCE: 15

Ser Tyr Trp Met His
1               5

<210> SEQ ID NO 16
<211> LENGTH: 17
<212> TYPE: PRT
<213> ORGANISM: Artificial Sequence
<220> FEATURE:
<221> NAME/KEY: DOMAIN
<223> OTHER INFORMATION: mAb1902 HCDR2

<400> SEQUENCE: 16

Met Ile His Pro Asn Ser Gly Ser Thr Asn Tyr Asn Glu Lys Phe Lys
1               5                   10                  15
Gly

<210> SEQ ID NO 17
<211> LENGTH: 9
<212> TYPE: PRT
<213> ORGANISM: Artificial Sequence
<220> FEATURE:
<221> NAME/KEY: DOMAIN
<223> OTHER INFORMATION: mAb1902 HCDR3

<400> SEQUENCE: 17

Leu Lys Thr Gly Asn Ser Phe Asp Tyr
1               5

<210> SEQ ID NO 18
<211> LENGTH: 17
<212> TYPE: PRT
<213> ORGANISM: Artificial Sequence
<220> FEATURE:
<221> NAME/KEY: DOMAIN
<223> OTHER INFORMATION: mAb1902 LCDR1

<400> SEQUENCE: 18

Lys Ser Ser Gln Ser Leu Leu Asn Ser Gly Asn Gln Lys Asn Tyr Leu
```

Thr

<210> SEQ ID NO 19
<211> LENGTH: 7
<212> TYPE: PRT
<213> ORGANISM: Artificial Sequence
<220> FEATURE:
<221> NAME/KEY: DOMAIN
<223> OTHER INFORMATION: mAb1902 LCDR2

<400> SEQUENCE: 19

Trp Ala Ser Thr Arg Glu Ser
1               5

<210> SEQ ID NO 20
<211> LENGTH: 9
<212> TYPE: PRT
<213> ORGANISM: Artificial Sequence
<220> FEATURE:
<221> NAME/KEY: DOMAIN
<223> OTHER INFORMATION: mAb1902 LCDR3

<400> SEQUENCE: 20

Gln Asn Ala Tyr Thr Tyr Pro Phe Thr
1               5

<210> SEQ ID NO 21
<211> LENGTH: 113
<212> TYPE: PRT
<213> ORGANISM: Artificial Sequence
<220> FEATURE:
<221> NAME/KEY: DOMAIN
<223> OTHER INFORMATION: VL1

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Ala Trp Tyr Gln Lys Pro Gly Gln
            35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys

<210> SEQ ID NO 22
<211> LENGTH: 113
<212> TYPE: PRT
<213> ORGANISM: Artificial Sequence
<220> FEATURE:
<221> NAME/KEY: DOMAIN
<223> OTHER INFORMATION: VL2

<400> SEQUENCE: 22

Asp Ile Val Met Thr Gln Ser Pro Asp Ser Leu Ala Val Ser Leu Gly
1               5                   10                  15

```
Glu Arg Ala Thr Ile Ser Cys Lys Ser Gln Ser Leu Leu Asn Ser
                20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Cys Gln Asn
                85                  90                  95

Asp Leu Tyr Tyr Pro Leu Thr Phe Gly Gln Gly Thr Lys Leu Glu Ile
                100                 105                 110

Lys
```

<210> SEQ ID NO 23
<211> LENGTH: 113
<212> TYPE: PRT
<213> ORGANISM: Artificial Sequence
<220> FEATURE:
<221> NAME/KEY: DOMAIN
<223> OTHER INFORMATION: VL3

<400> SEQUENCE: 23

```
Asp Ile Val Met Thr Gln Ser Pro Asp Ser Leu Ala Val Ser Leu Gly
 1               5                   10                  15

Glu Arg Ala Thr Ile Ser Cys Lys Ser Gln Ser Leu Leu Asn Ser
                20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Ile Tyr His Cys Gln Asn
                85                  90                  95

Asp Leu Tyr Tyr Pro Leu Thr Phe Gly Gln Gly Thr Lys Leu Glu Ile
                100                 105                 110

Lys
```

<210> SEQ ID NO 24
<211> LENGTH: 120
<212> TYPE: PRT
<213> ORGANISM: Artificial Sequence
<220> FEATURE:
<221> NAME/KEY: DOMAIN
<223> OTHER INFORMATION: VH1

<400> SEQUENCE: 24

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
                20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
 50                  55                  60

Lys Gly Arg Phe Thr Ile Ser Arg Asp Asn Ala Lys Asn Ser Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Gly Gly Tyr Asp Thr Arg Asn Ala Met Asp Tyr Trp Gly Gln
                    100                 105                 110

Gly Thr Thr Val Thr Val Ser Ser
            115                 120
```

<210> SEQ ID NO 25
<211> LENGTH: 120
<212> TYPE: PRT
<213> ORGANISM: Artificial Sequence
<220> FEATURE:
<221> NAME/KEY: DOMAIN
<223> OTHER INFORMATION: VH2

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Ile His Trp Val Arg Gln Ala Pro Gly Lys Gly Leu Glu Trp Val
            35                  40                  45

Ala Tyr Ile Ser Arg Gly Ser Ser Thr Ile Tyr Tyr Ala Asp Thr Val
        50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                    85                  90                  95

Ala Arg Gly Gly Tyr Asp Thr Arg Asn Ala Met Asp Tyr Trp Gly Gln
                    100                 105                 110

Gly Thr Thr Val Thr Val Ser Ser
            115                 120
```

<210> SEQ ID NO 26
<211> LENGTH: 120
<212> TYPE: PRT
<213> ORGANISM: Artificial Sequence
<220> FEATURE:
<221> NAME/KEY: DOMAIN
<223> OTHER INFORMATION: VH3

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Ile His Trp Val Arg Gln Ala Pro Gly Lys Gly Leu Glu Trp Ile
            35                  40                  45

Ala Tyr Ile Ser Arg Gly Ser Ser Thr Ile Tyr Tyr Ala Asp Thr Val
        50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                    85                  90                  95

Ala Arg Gly Gly Tyr Asp Thr Arg Asn Ala Met Asp Tyr Trp Gly Gln
                    100                 105                 110

Gly Thr Thr Val Thr Val Ser Ser
```

```
            115                 120

<210> SEQ ID NO 27
<211> LENGTH: 120
<212> TYPE: PRT
<213> ORGANISM: Artificial Sequence
<220> FEATURE:
<221> NAME/KEY: DOMAIN
<223> OTHER INFORMATION: VH4

<400> SEQUENCE: 27
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120

```
<210> SEQ ID NO 28
<211> LENGTH: 113
<212> TYPE: PRT
<213> ORGANISM: Artificial Sequence
<220> FEATURE:
<221> NAME/KEY: DOMAIN
<223> OTHER INFORMATION: VL11

<400> SEQUENCE: 28
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys

```
<210> SEQ ID NO 29
<211> LENGTH: 113
<212> TYPE: PRT
<213> ORGANISM: Artificial Sequence
<220> FEATURE:
<221> NAME/KEY: DOMAIN
<223> OTHER INFORMATION: VL12
```

<400> SEQUENCE: 29

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys

<210> SEQ ID NO 30
<211> LENGTH: 113
<212> TYPE: PRT
<213> ORGANISM: Artificial Sequence
<220> FEATURE:
<221> NAME/KEY: DOMAIN
<223> OTHER INFORMATION: VL13

<400> SEQUENCE: 30

Asp Ile Val Leu Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys

<210> SEQ ID NO 31
<211> LENGTH: 118
<212> TYPE: PRT
<213> ORGANISM: Artificial Sequence
<220> FEATURE:
<221> NAME/KEY: DOMAIN
<223> OTHER INFORMATION: VH11

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Met Ile His Pro Asn Ser Gly Ser Thr Asn Tyr Asn Glu Lys Phe
            50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Lys Thr Gly Asn Ser Phe Asp Tyr Trp Gly Gln Gly Thr
                100                 105                 110

Thr Val Thr Val Ser Ser
            115

<210> SEQ ID NO 32
<211> LENGTH: 118
<212> TYPE: PRT
<213> ORGANISM: Artificial Sequence
<220> FEATURE:
<221> NAME/KEY: DOMAIN
<223> OTHER INFORMATION: VH12

<400> SEQUENCE: 32

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Arg Leu Glu Trp Met
             35                  40                  45

Gly Met Ile His Pro Asn Ser Gly Ser Thr Asn Tyr Asn Glu Lys Phe
         50                  55                  60

Lys Gly Arg Val Thr Leu Thr Leu Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Lys Thr Gly Asn Ser Phe Asp Tyr Trp Gly Gln Gly Thr
                100                 105                 110

Thr Val Thr Val Ser Ser
            115

<210> SEQ ID NO 33
<211> LENGTH: 118
<212> TYPE: PRT
<213> ORGANISM: Artificial Sequence
<220> FEATURE:
<221> NAME/KEY: DOMAIN
<223> OTHER INFORMATION: VH13

<400> SEQUENCE: 33

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Arg Leu Glu Trp Ile
             35                  40                  45

Gly Met Ile His Pro Asn Ser Gly Ser Thr Asn Tyr Asn Glu Lys Phe
         50                  55                  60

Lys Gly Lys Ala Thr Leu Thr Leu Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

```
Ala Arg Leu Lys Thr Gly Asn Ser Phe Asp Tyr Trp Gly Gln Gly Thr
            100                 105                 110

Thr Val Thr Val Ser Ser
            115

<210> SEQ ID NO 34
<211> LENGTH: 118
<212> TYPE: PRT
<213> ORGANISM: Artificial Sequence
<220> FEATURE:
<221> NAME/KEY: DOMAIN
<223> OTHER INFORMATION: VH14

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser
            115

<210> SEQ ID NO 35
<211> LENGTH: 450
<212> TYPE: PRT
<213> ORGANISM: Artificial Sequence
<220> FEATURE:
<221> NAME/KEY: CHAIN
<223> OTHER INFORMATION: ch1901 heavy chain

<400> SEQUENCE: 35

Glu Val Gln Leu Met Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Ile His Trp Val Arg Gln Ala Pro Glu Met Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Tyr Asp Thr Arg Asn Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 36
<211> LENGTH: 220
<212> TYPE: PRT
<213> ORGANISM: Artificial Sequence
<220> FEATURE:
<221> NAME/KEY: CHAIN
<223> OTHER INFORMATION: ch1901 light chain

<400> SEQUENCE: 36

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln

```
                35                  40                  45

Pro Pro Lys Leu Leu Ile Tyr Gly Ala Ser Thr Arg Ala Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Ile Tyr His Cys Gln Asn
                 85                  90                  95

Asp Leu Tyr Tyr Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
210                 215                 220

<210> SEQ ID NO 37
<211> LENGTH: 448
<212> TYPE: PRT
<213> ORGANISM: Artificial Sequence
<220> FEATURE:
<221> NAME/KEY: CHAIN
<223> OTHER INFORMATION: ch1902 heavy chain

<400> SEQUENCE: 37

Glu Val Gln Leu Gln Glu Ser Gly Ala Glu Leu Val Lys Pro Gly Ala
1                5                  10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
         35                  40                  45

Gly Met Ile His Pro Asn Ser Gly Ser Thr Asn Tyr Asn Glu Lys Phe
 50                  55                  60

Lys Gly Lys Ala Thr Leu Thr Leu Asp Lys Ser Ser Ser Thr Ala Tyr
 65                  70                  75                  80

Met Gln Leu Ser Ser Leu Pro Ser Glu Asp Ser Ala Val Tyr Tyr Cys
                 85                  90                  95

Ala Arg Leu Lys Thr Gly Asn Ser Phe Asp Tyr Trp Gly Gln Gly Thr
                100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 38
<211> LENGTH: 220
<212> TYPE: PRT
<213> ORGANISM: Artificial Sequence
<220> FEATURE:
<221> NAME/KEY: CHAIN
<223> OTHER INFORMATION: ch1902 light chain

<400> SEQUENCE: 38

Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Thr Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
            210                 215                 220

<210> SEQ ID NO 39
<211> LENGTH: 220
<212> TYPE: PRT
<213> ORGANISM: Artificial Sequence
<220> FEATURE:
<221> NAME/KEY: CHAIN
<223> OTHER INFORMATION: L1

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
            210                 215                 220

```
<210> SEQ ID NO 40
<211> LENGTH: 220
<212> TYPE: PRT
<213> ORGANISM: Artificial Sequence
<220> FEATURE:
<221> NAME/KEY: CHAIN
<223> OTHER INFORMATION: L2

<400> SEQUENCE: 40

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 41
<211> LENGTH: 220
<212> TYPE: PRT
<213> ORGANISM: Artificial Sequence
<220> FEATURE:
<221> NAME/KEY: CHAIN
<223> OTHER INFORMATION: L3

<400> SEQUENCE: 41

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr His Cys Gln Asn
```

```
                    85                  90                  95
Asp Leu Tyr Tyr Pro Leu Thr Phe Gly Gln Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 42
<211> LENGTH: 450
<212> TYPE: PRT
<213> ORGANISM: Artificial Sequence
<220> FEATURE:
<221> NAME/KEY: CHAIN
<223> OTHER INFORMATION: H1

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

```
Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 43
<211> LENGTH: 450
<212> TYPE: PRT
<213> ORGANISM: Artificial Sequence
<220> FEATURE:
<221> NAME/KEY: CHAIN
<223> OTHER INFORMATION: H2

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 44
<211> LENGTH: 450
<212> TYPE: PRT
<213> ORGANISM: Artificial Sequence
<220> FEATURE:
<221> NAME/KEY: CHAIN
<223> OTHER INFORMATION: H3

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

-continued

```
               20                  25                  30
Gly Ile His Trp Val Arg Gln Ala Pro Gly Lys Gly Leu Glu Trp Ile
            35                  40                  45
Ala Tyr Ile Ser Arg Gly Ser Ser Thr Ile Tyr Tyr Ala Asp Thr Val
        50                  55                  60
Lys Gly Arg Phe Thr Ile Ser Arg Asp Asn Ala Lys Asn Ser Leu Tyr
65                  70                  75                  80
Leu Gln Met Thr Ser Leu Arg Ala Glu Asp Thr Ala Val Tyr Tyr Cys
                85                  90                  95
Ala Arg Gly Gly Tyr Asp Thr Arg Asn Ala Met Asp Tyr Trp Gly Gln
            100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
```

Gly Lys
    450

<210> SEQ ID NO 45
<211> LENGTH: 450
<212> TYPE: PRT
<213> ORGANISM: Artificial Sequence
<220> FEATURE:
<221> NAME/KEY: CHAIN
<223> OTHER INFORMATION: H4

<400> SEQUENCE: 45

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr

```
                   340               345               350
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 46
<211> LENGTH: 220
<212> TYPE: PRT
<213> ORGANISM: Artificial Sequence
<220> FEATURE:
<221> NAME/KEY: CHAIN
<223> OTHER INFORMATION: L11

<400> SEQUENCE: 46

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 47
<211> LENGTH: 220
```

<212> TYPE: PRT
<213> ORGANISM: Artificial Sequence
<220> FEATURE:
<221> NAME/KEY: CHAIN
<223> OTHER INFORMATION: L12

<400> SEQUENCE: 47

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 48
<211> LENGTH: 220
<212> TYPE: PRT
<213> ORGANISM: Artificial Sequence
<220> FEATURE:
<221> NAME/KEY: CHAIN
<223> OTHER INFORMATION: L13

<400> SEQUENCE: 48

Asp Ile Val Leu Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 49
<211> LENGTH: 448
<212> TYPE: PRT
<213> ORGANISM: Artificial Sequence
<220> FEATURE:
<221> NAME/KEY: CHAIN
<223> OTHER INFORMATION: H11

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Met Ile His Pro Asn Ser Gly Ser Thr Asn Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 50
<211> LENGTH: 448
<212> TYPE: PRT
<213> ORGANISM: Artificial Sequence
<220> FEATURE:
<221> NAME/KEY: CHAIN
<223> OTHER INFORMATION: H12

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Arg Leu Glu Trp Met
            35                  40                  45

Gly Met Ile His Pro Asn Ser Gly Ser Thr Asn Tyr Asn Glu Lys Phe
        50                  55                  60

Lys Gly Arg Val Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
```

```
            145                 150                 155                 160
        Ser Gly Ala Leu Thr Ser Gly Val His Thr Phe Pro Ala Val Leu Gln
                        165                 170                 175

Ser Ser Gly Leu Tyr Ser Leu Ser Ser Val Val Thr Val Pro Ser Ser
                        180                 185                 190

Ser Leu Gly Thr Gln Thr Tyr Ile Cys Asn Val Asn His Lys Pro Ser
                        195                 200                 205

Asn Thr Lys Val Asp Lys Lys Val Glu Pro Lys Ser Cys Asp Lys Thr
                        210                 215                 220

His Thr Cys Pro Pro Cys Pro Ala Pro Glu Leu Leu Gly Gly Pro Ser
        225                 230                 235                 240

Val Phe Leu Phe Pro Pro Lys Pro Lys Asp Thr Leu Met Ile Ser Arg
                        245                 250                 255

Thr Pro Glu Val Thr Cys Val Val Asp Val Ser His Glu Asp Pro
                        260                 265                 270

Glu Val Lys Phe Asn Trp Tyr Val Asp Gly Val Glu Val His Asn Ala
                        275                 280                 285

Lys Thr Lys Pro Arg Glu Glu Gln Tyr Asn Ser Thr Tyr Arg Val Val
                        290                 295                 300

Ser Val Leu Thr Val Leu His Gln Asp Trp Leu Asn Gly Lys Glu Tyr
        305                 310                 315                 320

Lys Cys Lys Val Ser Asn Lys Ala Leu Pro Ala Pro Ile Glu Lys Thr
                        325                 330                 335

Ile Ser Lys Ala Lys Gly Gln Pro Arg Glu Pro Gln Val Tyr Thr Leu
                        340                 345                 350

Pro Pro Ser Arg Asp Glu Leu Thr Lys Asn Gln Val Ser Leu Thr Cys
                        355                 360                 365

Leu Val Lys Gly Phe Tyr Pro Ser Asp Ile Ala Val Glu Trp Glu Ser
                        370                 375                 380

Asn Gly Gln Pro Glu Asn Asn Tyr Lys Thr Thr Pro Pro Val Leu Asp
        385                 390                 395                 400

Ser Asp Gly Ser Phe Phe Leu Tyr Ser Lys Leu Thr Val Asp Lys Ser
                        405                 410                 415

Arg Trp Gln Gln Gly Asn Val Phe Ser Cys Ser Val Met His Glu Ala
                        420                 425                 430

Leu His Asn His Tyr Thr Gln Lys Ser Leu Ser Leu Ser Pro Gly Lys
                        435                 440                 445

<210> SEQ ID NO 51
<211> LENGTH: 448
<212> TYPE: PRT
<213> ORGANISM: Artificial Sequence
<220> FEATURE:
<221> NAME/KEY: CHAIN
<223> OTHER INFORMATION: H13

<400> SEQUENCE: 51

Glu Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Ser Tyr
                        20                  25                  30

Trp Met His Trp Val Arg Gln Ala Pro Gly Gln Arg Leu Glu Trp Ile
                        35                  40                  45

Gly Met Ile His Pro Asn Ser Gly Ser Thr Asn Tyr Asn Glu Lys Phe
                        50                  55                  60
```

-continued

Lys Gly Lys Ala Thr Leu Thr Leu Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 52
<211> LENGTH: 448
<212> TYPE: PRT
<213> ORGANISM: Artificial Sequence
<220> FEATURE:
<221> NAME/KEY: CHAIN

<223> OTHER INFORMATION: H14

<400> SEQUENCE: 52

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 53
<211> LENGTH: 448
<212> TYPE: PRT
<213> ORGANISM: Artificial Sequence
<220> FEATURE:
<221> NAME/KEY: CHAIN
<223> OTHER INFORMATION: IMAB-362 heavy chain

<400> SEQUENCE: 53

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 54
<211> LENGTH: 220
<212> TYPE: PRT
<213> ORGANISM: Artificial Sequence
<220> FEATURE:
<221> NAME/KEY: CHAIN
<223> OTHER INFORMATION: IMAB-362 light chain

<400> SEQUENCE: 54

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```